(12) United States Patent
Busch et al.

(10) Patent No.: US 10,357,569 B2
(45) Date of Patent: Jul. 23, 2019

(54) COMPOSITIONS CONTAINING CARBOHYDRATE PARTIAL ESTER

(71) Applicant: BASF SE, Ludwigshafen (DE)

(72) Inventors: Stefan Busch, Düsseldorf (DE); Eike Ulf Mahnke, Xanten (DE); Melina Machado Sincero, Düsseldorf (DE); Markus Kloeker, Düsseldorf (DE)

(73) Assignee: BASF SE, Ludwigshafen (DE)

( * ) Notice: Subject to any disclaimer, the term of this patent is extended or adjusted under 35 U.S.C. 154(b) by 0 days.

(21) Appl. No.: 15/534,517

(22) PCT Filed: Dec. 11, 2015

(86) PCT No.: PCT/EP2015/079472
§ 371 (c)(1),
(2) Date: Jun. 9, 2017

(87) PCT Pub. No.: WO2016/092088
PCT Pub. Date: Jun. 16, 2016

(65) Prior Publication Data
US 2017/0360938 A1    Dec. 21, 2017

(30) Foreign Application Priority Data

Dec. 12, 2014    (EP) .................................. 14197689

(51) Int. Cl.
| | | |
|---|---|---|
| *A61K 47/26* | (2006.01) | |
| *A61K 47/14* | (2017.01) | |
| *A61K 8/37* | (2006.01) | |
| *A61K 8/60* | (2006.01) | |
| *A61K 8/36* | (2006.01) | |
| *A61Q 19/00* | (2006.01) | |
| *A23L 33/125* | (2016.01) | |

(52) U.S. Cl.
CPC ............ *A61K 47/26* (2013.01); *A23L 33/125* (2016.08); *A61K 8/361* (2013.01); *A61K 8/37* (2013.01); *A61K 8/375* (2013.01); *A61K 8/60* (2013.01); *A61K 47/14* (2013.01); *A61Q 19/00* (2013.01); *A23V 2002/00* (2013.01)

(58) Field of Classification Search
CPC .......... A61K 47/26; A61K 47/14; A61K 8/37; A61K 8/60; A61Q 19/00; A23L 33/125; A23V 2002/00
USPC .................................................. 424/401, 59
See application file for complete search history.

(56) References Cited

U.S. PATENT DOCUMENTS

| | | | |
|---|---|---|---|
| 5,945,519 A | | 8/1999 | Desai et al. |
| 6,831,107 B2 * | | 12/2004 | Dederen ................ A61K 8/062 |
| | | | 424/401 |
| 2008/0108578 A1 | | 5/2008 | Le Hen Ferrenbach et al. |
| 2012/0115949 A1 * | | 5/2012 | Beuche .................... A61K 8/37 |
| | | | 514/552 |

FOREIGN PATENT DOCUMENTS

| | | |
|---|---|---|
| DE | 10 2004 054 432 A1 | 7/2005 |
| EP | 885 898 A2 | 12/1998 |
| EP | 1 787 628 A1 | 5/2007 |
| EP | 1 811 951 A2 | 8/2007 |
| GB | 1399053 A | 6/1975 |
| GB | 1499989 A | 2/1978 |
| JP | 3836162 B2 | 10/2006 |
| WO | WO-90/11285 A1 | 10/1990 |
| WO | WO-2014/090959 A1 | 6/2014 |

OTHER PUBLICATIONS

International Search Report for Patent Application No. PCT/EP2015/079472, dated Feb. 26, 2016 (English translation).

* cited by examiner

*Primary Examiner* — Yih-Horng Shiao
(74) *Attorney, Agent, or Firm* — Marshall, Gerstein & Borun LLP

(57) ABSTRACT

The present invention relates to a composition containing carbohydrate partial esters, the preparation thereof and products containing the carbohydrate partial esters according to the invention.

20 Claims, 3 Drawing Sheets

COMPOSITIONS CONTAINING CARBOHYDRATE PARTIAL ESTER

CROSS-REFERENCE TO RELATED APPLICATIONS

Figure 1:
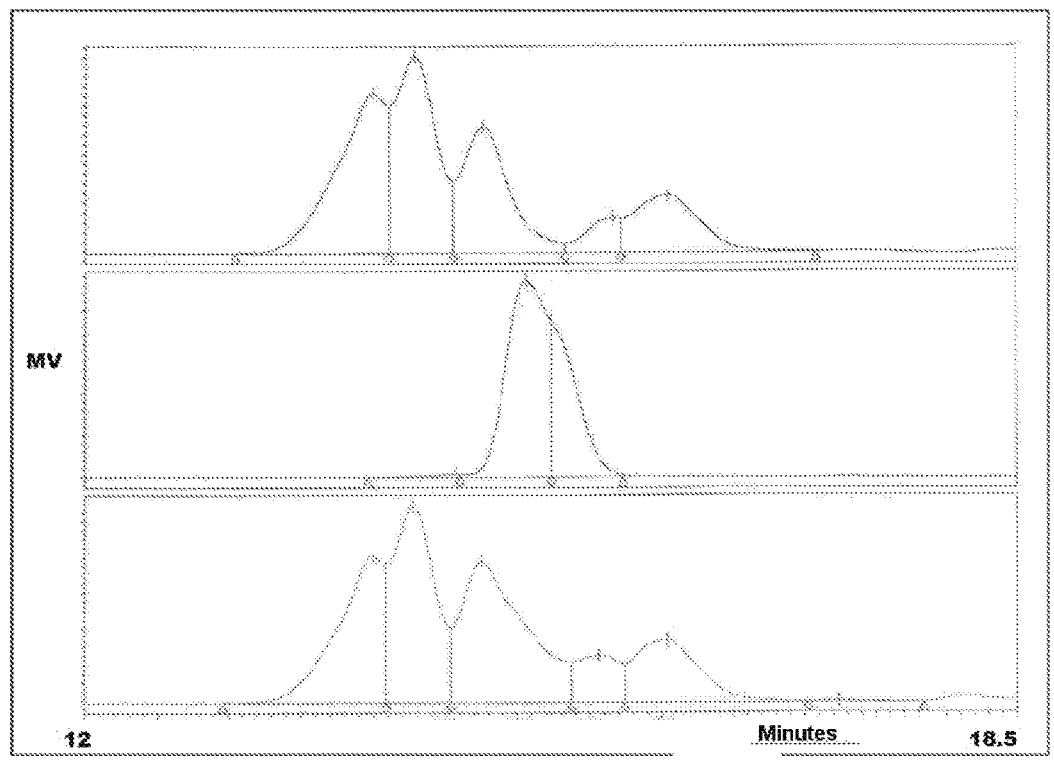

This application is the U.S. National Stage application of International Patent Application No. PCT/EP2015/079472, filed Dec. 11, 2015, which claims the benefit of European Patent Application No. 14197689.4, filed Dec. 12, 2014.

The present invention relates to a composition containing carbohydrate partial esters, the preparation thereof and products containing the carbohydrate partial esters according to the invention.

Processes for the preparation of carbohydrate partial esters are known from EP 1 811 951 A1, EP 0 885 898 B1, GB 1 399 053 and GB 1 499 989. The preparation is based substantially on a catalyzed transesterification of carbohydrates with fatty acid alkyl esters or glycerides. The purification or working up of the crude product after the transesterification is described in WO 90 11285 A or JP 383 6162 B2.

The carbohydrate partial esters are conventionally prepared in the presence of an alkaline catalyst by transesterification of glycoses with fatty acid methyl esters at temperatures of 120-160° C. After addition of solvents and/or emollients, the unreacted sugar is separated off by decanting and filtration after cooling to 60-130° C.

For an efficient working up, auxiliary substances which lead to a reduction in the viscosity and as a result also render possible a rapid separating off of the residual sugar by decanting and filtering at lower temperatures are conventionally added to the crude product. Inert hydrocarbons, such as hydrogenated polyisobutene, are preferably employed here. If the auxiliary substances (emollients) employed for reducing the viscosity are reactive under the working up conditions, complete deactivation of the transesterification catalyst is necessary. Emollients which are reactive under the working up conditions are, for example, fatty alcohols or ester oils. If the catalyst is not completely deactivated, further transesterification reactions take place, so that a change in the distribution of the carbohydrate partial esters is to be found.

Furthermore, there are also present in the crude product unreacted fatty acid esters, such as e.g. the fatty acid methyl esters described above or other ester oils with short-chain alcohol components, which on the basis of their reactivity are employed as educts in the synthesis of carbohydrate partial esters.

The use of esters with longer-chain alcohol components as emollients on the one hand lowers the reactivity towards a transesterification during the working up, but on the other hand the viscosity is increased. Due to the increase in the viscosity, the working up, in particular the filtration, must be carried out at significantly higher temperatures. In order to avoid a higher temperature and to lower the viscosity, the content of emollients must be increased further. Both an increase in the viscosity and an increase in the content of emollients lower the efficiency of the working up steps. Generally, emollients from hydrocarbons adversely influence the properties of pastilles.

Furthermore, from the process technology aspect a complete deactivation of the catalyst is difficult to achieve and represents an additional process step. Since alkaline transesterification catalysts are conventionally employed, the deactivation is carried out by addition of acid and is often achieved only incompletely.

The addition of auxiliary substances, such as e.g. the abovementioned additional emollients or acid, adversely influence the color and the acid content of the crude product.

The object of the present invention was to overcome the disadvantages of the prior art, in particular with respect to the working up of the crude product.

A process for the preparation of carbohydrate partial esters and for working up the crude product which is highly efficient due to a small number of working steps is to be provided for this. This should be a solvent-free and low-waste process.

It was of particular importance here that the distribution of the carbohydrate partial esters of the crude product after the synthesis of the carbohydrate partial ester mixture has ended does not differ from the distribution of the carbohydrate partial esters in the purified or worked up end product. In the process, moreover, by the emollients employed a viscosity is to be reached which on the one hand renders possible an efficient separating off of the residual sugar (unreacted carbohydrates) by filtration and/or decanting, preferably in only one separation step. On the other hand a (partial) dissolving of the residual sugar in relatively large amounts due to the higher polarity of the diluent compared with hydrocarbons is to be avoided.

A further object of the present invention was to provide a composition containing carbohydrate partial esters. The composition is to have a precisely defined partial ester distribution which does not change by working up or storage. Furthermore, with respect to color, stability and viscosity the composition is to meet all the requirements for a direct further process, in particular for a use in cosmetic or pharmaceutical formulations. Preferably, the composition is to consist substantially or exclusively of sustainable raw materials. Hydrocarbons of petrochemical origin are to be avoided or are not to be contained therein. Moreover, shaped bodies containing the composition according to the invention or substantially consisting thereof are to have a better shelf life with respect to consistency, color and odor. The shaped bodies must the sufficiently hard and are not to stick together, in order to avoid caking even during relatively long storage. The emollient should not emerge from the shaped body even under unfavorable storage conditions, such as e.g. elevated temperature. Brittle shaped bodies have a reduced stability and lead to formation of dust. An addition of additional auxiliary substances, in particular for stabilizing the shaped bodies, is to be avoided.

These objects are achieved by a composition, shaped body and the process according to the claims.

The present invention provides a composition containing:
   a1) carbohydrate partial esters as the product of an esterification of at least one carbohydrate with acyl components of the formula R1-COO,
   b1) alkyl esters of the formula R1-COO—R2 and
   c1) ester oils of the formula R1-COO—R3,
and optionally one or more compounds selected from the group containing or consisting of: carbohydrates, fatty acids, fatty soaps, water and catalyst;
wherein the ester oils c1) have an alcohol component R3 selected from the group of
i) branched and unbranched alcohols with C8-C22, preferably C10-C20, particularly preferably C12 or C14 to C20, in particular C16 and/or C18 or
ii) polyalcohols or
iii) mixtures thereof
which are completely esterified with an acyl component R1 selected from the group of mono- and di-acids of chain length C6-C22, preferably C10-C20, particularly preferably C12 or C14 to C20, in particular C16 and/or C18 or any desired combinations.

The present invention also provides a composition containing:
a2) carbohydrate partial esters having an average degree of esterification of 1-4,
b2) organic alkyl esters with an acyl component having 6-22 carbon atoms, preferably C10-C20, particularly preferably C12 or C14 to C20, in particular C16 and/or C18,
c2) ester oils with a linear acyl component having 6-22 carbon atoms, preferably C10-C20, particularly preferably C12 or C14 to C20, in particular C16 and/or C18 and a linear alcohol component having 8-22 carbon atoms, preferably C10-C20, particularly preferably C12 or C14 to C20, in particular C16 and/or C18, and optionally one or more compounds selected from the group containing or consisting of: carbohydrates, fatty acids, fatty soaps, water and catalyst.

In one embodiment the composition according to the invention contains:
a) carbohydrate partial esters having an average degree of esterification of 1-4 in a proportion of 50-90%, preferably 55-80%, particularly preferably 55-70%, in particular 55-65%,
b) organic alkyl esters with an acyl component having 6-30 carbon atoms in a proportion of 0-10%, preferably 2.5-7.5%, particularly preferably 3-5%, in particular 4% or 5%;
c) ester oils in a proportion of 5-30%, preferably 10-20%, particularly preferably 12-17%, in particular 15%;
and optionally carbohydrates (residual sugars) in a proportion of 0-10%, preferably 3-8%, in particular 3-5%; and/or optionally fatty soaps in a proportion of 0-20%, preferably 1-15%, particularly preferably 5-12%, in particular 10% or 12% and/or optionally
fatty acids: 0-10%, preferably 2.5-7.5, particularly preferably 3-5%, in particular 4% or 7%.

The compounds or components a), b) and c) in each case represent a1) and/or a2), b1) and/or b2) or, respectively, c1) and/or c2).

The composition according to the invention can contain water in a proportion of 5%, preferably 2%, particularly preferably 1%, in particular 0.5-1% or less or can be substantially or completely anhydrous. "Substantially anhydrous" means that the water content of the composition is <5 wt. %, by preference <2 wt. %, preferably <1 wt. % and in particular <0.1 wt. %. "Completely anhydrous" means that the water content is below the detection limits of conventional and known methods for the quantitative determination of water.

The composition according to the invention can contain carbohydrates (residual sugars) in a proportion of 5%, preferably 2%, particularly preferably 1%, in particular 0.5% or less or can be substantially or completely free from carbohydrates. "Substantially free from carbohydrates" means that the carbohydrate content of the composition is <5 wt. %, by preference <2 wt. %, preferably <1 wt. % and in particular <0.1 wt. %. "Completely free from carbohydrates" means that the carbohydrate content is below the detection limits of conventional and known methods for the quantitative determination of water.

The total of the compounds or components of the composition according to the invention is in each case 100%.

In one embodiment the product a1) or a2) is a carbohydrate partial ester of a glycose with an acyl component of b1) or b2).

Glycoses includes the polyhydroxy aldehydes (aldoses) and polyhydroxy ketones (ketoses), also called carbohydrates, as well as higher molecular weight compounds which can be converted into such substances by hydrolysis. In the context of the invention both the monomeric polyhydroxy aldehydes or polyhydroxy ketones (monosaccharides) or their dimers to decamers (disaccharides, trisaccharides, oligosaccharides) can be employed as glycoses. Possible monosaccharides (also called "simple sugars") are, for example, bioses, trioses, tetraoses, pentoses, hexoses, heptoses etc. Typical examples of aldopentoses are D-ribose, D-xylose and L-arabinose. The most important aldohexoses include D-glucose, D-mannose and D-galactose; of the ketohexoses, D-fructose and sorbose are to be mentioned. The 6-deoxy sugars L-fucose and L-rhamnose are likewise widely used hexoses and are likewise possible starting substances. The simplest oligosaccharides which are suitable as starting substances are the disaccharides. Preferably, sucrose (cane sugar, beet sugar), lactose (milk sugar) and/or maltose (malt sugar) are employed.

The use of mono- and/or disaccharides is preferred in the context of the process; in particular, saccharose (sucrose) or glucose are preferably employed.

In one embodiment of the present invention the alcohol component of the ester b1) or b2) is a C1 to C3 alcohol unit, preferably methyl and/or ethyl.

In one embodiment at least one alkyl ester b2) and/or b1) with an acyl component selected from the group of aliphatic, linear or branched acyl radicals having 6 to 22 carbon atoms and 0 and/or 1, 2 or 3 double bonds is present. Furthermore, the acyl component is selected from the group containing the acyl radicals of caproic acid, caprylic acid, 2-ethylhexanoic acid, capric acid, lauric acid, isotridecanoic acid, myristic acid, palmitic acid, palmoleic acid, stearic acid, isostearic acid, oleic acid, elaidic acid, petroselinic acid, linoleic acid, linolenic acid, elaeostearic acid, arachic acid, gadoleic acid, behenic acid and erucic acid and technical grade mixtures thereof with methanol, ethanol, propanol, isopropyl alcohol, n-butanol, i-butanol, tert-butanol, n-pentanol and isopentanol or technical grade mixtures thereof which are obtained e.g. in the pressure cracking of natural fats and oils, in the reduction of aldehydes from Roelen's oxo synthesis or dimerization of unsaturated fatty acids. Technical grade fatty acids having 12 to 18 carbon atoms, such as, for example, coconut, palm, palm kernel or tallow fatty acid, are preferred.

In one version alkyl esters b1) and/or b2) with linear, saturated acyl radicals having 12 to 30 C atoms, preferably having 16 to 24 C atoms are employed. C16-C24-fatty acid methyl esters, in particular C16-C20-fatty acid methyl esters are preferred, linear and unbranched esters among these being particularly preferred according to the invention. The use of C16-fatty acid methyl esters and/or C18-fatty acid methyl esters or of any desired mixtures of C16/C18-fatty acid methyl esters, for example having a C16/C18 content of 50:50, 40:60, 30:70, 60:40 or 70:30 is advantageous according to the invention.

In a preferred embodiment of the process according to the invention and of the composition and shaped bodies according to the invention all the components, that is to say the carbohydrate partial esters a), the alkyl esters b) and the ester oils c) thus have the same acyl component R1, namely a mixture of fatty acid radicals having a carbon length of C16 and C18.

In one version an ester of isostearic acid is employed.

The molar use ratio employed of alkyl ester:carbohydrate is preferably at least 0.5, in particular 0.5-2.5 and particularly preferably 0.6-2.0. At lower molar ratios the reaction products are increasingly colored and viscous, which presumably is to be attributed to a caramelization of the sugar. A molar ratio of 1.3-1.6, in particular 1.4-1.55 is particularly preferred according to the invention in order to reduce caramelization of the sugar and to obtain crude products which are lighter in color.

In a further embodiment at least one acyl component of the ester a1), b1), c1), a2), b2) or c2) is a fatty acid radical having 16 and/or 18 carbon atoms.

In one alternative all the acyl components of the esters a1), b1), c1), a2), b2) or c2) are identical.

In a further alternative all the acyl components of the esters a1), b1), c1), a2), b2) or c2) are fatty acid radicals having 16 and/or 18 carbon atoms, preferably all are identical.

One embodiment of the present invention relates to a composition, characterized in that the alcohol component of the ester oils c1) or c2) is a fatty alcohol having 16 and/or 18 carbon atoms or a Guerbet alcohol having 16 to 20 carbon atoms.

In one alternative cetyl palmitate (for example Cutina CP) is employed as the ester oil c1) and/or c2).

In a further alternative cetyl palmitate (for example Cutina CP), Guerbet hexyldecyl stearate (for example Eutanol G16S) and/or hydrogenated palm fat triglycerides (for example Waretta 863) are employed as ester oils c1). Hydrogenated palm fat is obtained by (partial) hydrogenation of the double bonds of unsaturated fatty acids in the corresponding oil and are distinguished inter alia by an elevated melting point and improved stability to oxidation.

One alternative of the composition is characterized in that the alcohol component of the ester oils c1) or c2) is a polyalcohol selected from the group containing/consisting of: ethylene glycol, propylene glycol, butylene glycol, neopentyl glycols (NPG, TMP, PE), glycerol. Neopentyl glycols which can be employed are 2,2-dimethyl-1,3-propanediol=NPG, trimethylolpropane=TMP or pentaerythritol=PE.

Preferably, the polyalcohols are completely esterified. In one embodiment glycerol is employed in the completely esterified form.

In one version an aliphatic, linear or branched hydrocarbon radical having 6 to 22 carbon atoms and 0 and/or 1, 2 or 3 double bonds can be employed according to the invention as the alcohol component.

Fatty and/or Guerbet alcohols selected from the group containing or consisting of: C16- and/or C18-fatty alcohol, C16-, C18- and/or C20-Guerbet alcohol, are preferred.

In one alternative the alcohol component is selected from the group containing or consisting of: caproyl alcohol, capryl alcohol, 2-ethylhexyl alcohol, capric alcohol, 2-propylheptyl alcohol, lauryl alcohol, isotridecyl alcohol, myristyl alcohol, cetyl alcohol, palmoleyl alcohol, stearyl alcohol, isostearyl alcohol, oeyl alcohol, elaidyl alcohol, petroselinyl alcohol, linoleyl alcohol, linolenyl alcohol, elaeostearyl alcohol, arachyl alcohol, gadoleyl alcohol, behenyl alcohol, erucyl alcohol and brassidyl alcohol and technical grade mixtures thereof which are obtained e.g. in the high pressure hydrogenation of technical grade methyl esters based on fats and oils or aldehydes from the Roelen's oxo synthesis and as a monomer fraction in the dimerization of unsaturated fatty alcohols. Technical grade fatty alcohols having 12 to 18 carbon atoms, such as, for example, coconut, palm, palm kernel or tallow fatty alcohol, are preferred.

In one version the composition contains no free alcohol component of the ester oil.

In one version the composition contains no free partial glycerides of the ester oil.

In a further embodiment the composition according to the invention contains various carbohydrate partial esters.

In One Alternative monoesters are present in a proportion of 0%-20%, preferably 5-15%, particularly preferably 7-12%, in particular 7% or 8%;

diesters are present in a proportion of 10%-40%, preferably 20-35%, particularly preferably 25-30%, in particular 24% or 27%;

triesters are present in a proportion of 20%-50%, preferably 30-45%, particularly preferably 35-40%, in particular 33% or 37% and tetraesters and higher esters are present in a proportion of 15%-40%, preferably 20-40%, particularly preferably 25-35%, in particular 26% or 29%, wherein the sum is 100%.

In a further alternative the ratio of monoester:diester:triester:tetraester is between 0.5 and 1.5:between 3.0 and 4.0:between 4.0 and 5.0:between 3.0 and 4.0, preferably 1:3.5:4.7:3.7, particularly preferably 1:3.4:(4.6 or 4.7):(3.6 or 3.7).

In one embodiment the carbohydrate partial ester distribution is determined by means of GPC. The determination is preferably carried out as follows:

Principle: The sample is dissolved in tetrahydrofuran, separated by means of liquid chromatography and detected with an RI detector. The area percentage quantification is based on the evaluation method according to the Ph.Eur. monograph of glycerol monostearate type II, method 2.2.30, and DGF C-VI 5b (02)

Equipment: HPLC system with RI detector e.g. Acquity System from Waters; RI detector; Empower evaluation software; 2+PLgel 5 µm 100 A 30 cm*8 mm Dr. Maisch HPLC Conditions:

| | |
|---|---|
| Separating column | PLgel 5 µm 100 A 30 cm * 8 mm Dr. Maisch |
| Eluent | Tetrahydrofuran |
| Flow rate | 1.0 ml/min at 25° C. isocratic |
| Injector | 50 µl |
| Detector | RI at 40° C. |

Determination Procedure:

On an analytical balance approx. 0.5 g of the sample is weighed analytically accurately into a 50 ml volumetric flask and acidified with formic acid. The volumetric flask is topped up to the mark with tetrahydrofuran. The mixture is to be homogenized by shaking.

The viscosity of the worked up composition according to the invention is 0.5 to 3 Pa s, preferably 1.0 to 2.0, particularly preferably 1.2 to 1.5, in particular 1.3 Pa s at 100° C. and a shear rate of 100/s.

The viscosity is determined in dynamic flow equilibrium at 100° C. and a shear rate of 100/s, in one version by means of a V-VOR 120 rheometer (cone/plate viscometer with 4° and 40 mm) from Bohlin.

The present invention also provides a shaped body containing or consisting of the composition according to the invention.

The shaped bodies according to the invention can contain further carbohydrate partial esters in addition to the composition according to the invention. In one alternative they additionally contain an emollient for carbohydrate partial esters which is suitable for cosmetic uses and/or 1-10 wt. % of a C16-C40-fatty alcohol or of any desired mixture of these fatty alcohols, wherein the content of further auxiliary substances and additives is at most 20 wt. %.

For further processing in one embodiment carbohydrate partial esters are dissolved in a C16-C40-fatty alcohol, preferably a C18-C30- and particularly preferably a C20-C24-fatty alcohol or any desired mixture of these fatty alcohols.

In one alternative the composition according to the invention and/or the shaped body according to the invention contains no C16-C40-fatty alcohol, preferably no C18-C30- and particularly preferably no C20-C24-fatty alcohol or no any desired mixture of these fatty alcohols.

A preferred embodiment of the shaped body contains 10-95 wt. % of a carbohydrate partial ester or of a mixture of carbohydrate partial esters a), 5-20 wt. % of an emollient suitable for cosmetic uses, preferably ester oils c) and auxiliary substances and additives, wherein the content of further auxiliary substances and additives is at most 10 wt. %. Preferably, the content of further auxiliary substances and additives is less than 10 wt. %, in particular less than 5 wt. % of the total composition. Very particularly preferably, the proportion of further auxiliary substances and additives is limited merely to by-products which are contained in the product mixture as a result of the reaction.

The shaped bodies are storage-stable and show no "sweating", even during storage for longer than one week, preferably 1 month, particularly preferably 6 months, in particular 1 year at 40° C., i.e. no separation of liquid product constituents which leads to formation of a (continuous) film of liquid on the pastille surface or on container walls occurs. "Sweating" is undesirable because it makes processing of the product difficult and impairs the appearance thereof.

To investigate the shelf life, 15 ml of pastilles were introduced into a steel cylinder and loaded with a test stamp weighing 900 g and stored in this arrangement for one day at 40° C. If the shelf life is good the test specimen obtained disintegrates at room temperature without a great action of external force.

In one alternative the shaped body is a pastille and/or flakes.

Pastilles consist of solidified melts or solid solutions in a single-dosed form. They have a different structure to tablets, which are produced under pressing pressure from powders or granules on tablet presses, or to coated tablets, which is a formulation provided with a coating. Pastilles are produced by pouring a liquid into prefabricated powder moulds. The still liquid pastille precursors are then gently cooled until they solidify.

In a preferred form the melt of the product is made into pastilles in a cooling conveyor belt installation by being applied to a belt as drops and being cooled during transportation until solidification is complete.

A further preferred form of shaped bodies are flakes. The flaking is carried out, for example, with a flaking roll: The melt is applied in a thin layer to a cooled rotating roll, where it solidifies completely in the course of the rotation. The solid product is detached continuously from the roll by means of fixed scrapers and thereby breaks up into small plates, so-called flakes.

The present invention also provides a process for the preparation of the composition according to the invention or of the shaped body according to the invention, characterized by the following steps:
i) esterification of a carbohydrate with an alkyl ester b1) or b2) in the presence of a catalyst,
ii) addition of ester oils c1) or c2),
iii) separating off of the crude product from the residual sugar, optionally
iv) bleaching of the liquid phase separated off and optionally
v) production of a shaped body.

In one alternative the process according to the invention can comprise further steps.

In a further alternative the process is characterized by the steps described above and comprises no further steps.

In one embodiment the process is a solvent-free process for the preparation of carbohydrate partial esters having an average degree of esterification in the range of from 1 to 4 by alkali-catalyzed esterification or transesterification in the presence of a catalyst mixture of alkali metal carbonate and alkali metal hypophosphite, wherein
i-1) for formation of a catalytically active system at least one alkali metal carbonate and at least one alkyl ester b1) and/or b2) are mixed and
i-2) carbohydrates preferably having 5 to 12 carbon atoms, optionally carbohydrate partial esters as emulsifiers and alkali metal hypophosphite are added to the mixture resulting from i-1) with constant stirring, so that a dispersion results, and the corresponding alkyl alcohol is removed from the resulting mixture with constant stirring at temperatures of up to 100° C. under a pressure of up to 50 mbar and
i-3) the esterification or transesterification reaction is continued under a pressure of up to 50 mbar and at temperatures of up to 125° C. with constant stirring until the content of alkyl esters b1) and/or b2) has fallen to at least 8 wt. %, based on the total composition,
wherein steps i-1) to i-3) are optionally carried out under an inert gas atmosphere.

In the process according to the invention the catalyst combination of alkali metal carbonate and alkali metal hypophosphite delivers products of improved color in good yields and comparatively shorter reaction times, which have a relatively low ash content. In addition, the formation of by-products, such as soap, is reduced. Nitrogen is preferably employed as the inert gas. The use of inert gases delivers products still lighter in color The reaction takes place in the absence of solvents, which is of considerable advantage both from the economic aspect and with respect to a use in the cosmetics sector. A further unexpected advantage of the process is that in spite of the reduction of the alkali metal catalyst an effective reaction is achieved with an improved color quality in comparatively short reaction times.

In one alternative the process according to the invention is carried out analogously to the process described in WO 2006/050832 A2, the disclosure of which is included herewith by reference.

A combination of alkali metal carbonate(s) and alkali metal hypophosphite(s) is used according to the invention as catalysts. Preferably, sodium and/or potassium carbonate is employed, and sodium and/or potassium hypophosphite. It is advantageous according to the invention to employ 0.06-0.6 mol of alkali metal carbonate and 0.01-0.1 mol of alkali metal hypophosphite per mol of glycose. Amounts employed of 0.07-0.3 mol of potassium carbonate and 0.01-0.05 mol of sodium hypophosphite per mol of glycose, in particular 0.08-0.2 mol of potassium carbonate and 0.01-0.03 mol of sodium hypophosphite per mol of glycose, and very particularly preferably 0.1-0.15 mol of potassium carbonate and 0.012-0.02 mol of sodium hypophosphite per mol of glycose have proved to be particularly advantageous according to the invention.

In the context of the invention it has proved particularly advantageous to employ as emulsifiers partial esters of carbohydrates, the carbohydrate unit of which is identical to those of the target products. It is particularly advantageous according to the invention to employ carbohydrate partial esters in which both the carbohydrate unit and the ester radical coincide with those of the target products, that is to say which optionally differ only by the degree of esterification. The use of sucrose partial esters having an average degree of esterification in the range of from 2 to 6, in particular from 3 to 4 is particularly preferred. Suitable sugar esters are, for example, Sisterna® SP 01, Sisterna® SP 30 and Sisterna® SP 50. Emulsifiers which are preferred according to the invention are sugar esters having a low proportion of monoester, preferably a proportion of monoester of less than 30 wt. % and in particular a proportion of monoester of less than 1 wt. %. The use of partial esters of sucrose with C16/C18-fatty acids which have a correspondingly low proportion of monoester is particularly preferred according to the invention since these lower the reaction time and contribute towards a fast reaction. The carbohydrate partial esters can be employed as a powder, in liquid form, but also in pelleted form. It has thus proved advantageous, for example, to employ pellets of sucrose partial esters with those fatty acid methyl esters which are also used as reactants.

Possible additional co-emulsifiers are e.g. nonionic surfactants from at least one of the following groups:
(1) addition products of from 2 to 30 mol of ethylene oxide and/or 0 to 5 mol of propylene oxide on linear fatty alcohols having 8 to 22 C atoms, on fatty acids having 12 to 22 C atoms and on alkylphenols having 8 to 15 C atoms in the alkyl group and alkylamines having 8 to 22 carbon atoms in the alkyl radical;
(2) C2-C18-fatty acid mono- and diesters of addition products of from 1 to 30 mol of ethylene oxide on glycerol;
(3) glycerol mono- and diesters and sorbitan mono- and diesters of saturated and unsaturated fatty acids having 6 to 22 carbon atoms and ethylene oxide addition products thereof;
(4) alkyl mono- and oligoglycosides having 8 to 22 carbon atoms in the alkyl radical and ethoxylated analogues thereof;
(5) addition products of from 15 to 60 mol of ethylene oxide on castor oil and/or hydrogenated castor oil;
(6) polyol and in particular polyglycerol esters, such as e.g. polyglycerol polyricinoleate or polyglycerol poly-12-hydroxystearate. Mixtures of compounds from several of these substance classes are likewise suitable;
(7) addition products of from 1 to 15 mol of ethylene oxide on castor oil and/or hydrogenated castor oil;
(8) partial esters based on linear, branched, unsaturated or saturated C6/C22 fatty acids, ricinoleic acid and 12-hydroxystearic acid and glycerol, polyglycerol, pentaerythritol, dipentaerythritol, sugar alcohols (e.g. sorbitol), alkyl glucosides (e.g. methyl glucoside, butyl glucoside, lauryl glucoside) and polyglucosides (e.g. cellulose);
(9) mono-, di- and trialkyl phosphates and mono-, di- and/or tri-PEG-alkyl phosphates and salts thereof;
(10) wool wax alcohols;
(11) polysiloxane/polyalkyl polyether copolymers and corresponding derivatives;
(12) mixed esters of pentaerythritol, fatty acids, citric acid and fatty alcohol according to and/or mixed esters of fatty acids having 6 to 22 carbon atoms, methylglucose and polyols, preferably glycerol and
(13) polyalkylene glycols.

The molar ratio employed of carbohydrate partial ester as an emulsifier: carbohydrate employed as an educt is preferably 0.03-0.25, preferably 0.04-0.2 and particularly preferably 0.09-0.12.

A process which is preferred according to the invention is that in which the molar ratio of alkali metal carbonate:alkyl ester b1) and/or b2): carbohydrate employed as an educt: carbohydrate partial ester as an emulsifier: alkali metal hypophosphite varies in the range of (0.06-0.6):(0.6-2.0):1: (0.04-0.2):(0.01-0.1).

The reaction is carried out by a procedure in which an emulsion/dispersion which contains the catalyst system, the carbohydrates and the carbohydrate esters and optionally further emulsifiers is prepared by vigorous stirring. In the case of medium- to high-viscosity mixtures the mechanical stirring is carried out on an industrial scale with a stirrer system of an impeller stirrer in combination with baffles at speeds of rotation of from 50 to 400 revolutions per minute, preferably 100-300 revolutions per minute.

Preferably, the pressure in step i-2) and step i-3) is at most 25 mbar and very particularly preferably at most 15 mbar, in particular at most 10 mbar. These pressure conditions ensure that water is removed from the reaction equilibrium as efficiently as possible. In particular, the "predrying" in step i-2) is intended to remove the residual water caused by the raw materials. Step i-2) is preferably carried out at temperatures of 70-85° C., in particular 75-80° C. and under a pressure of from 1 to 25 mbar, preferably 1 to 15 mbar. The actual esterification reaction, step i-3), is preferably carried out at temperatures of 100° C.-125° C., in particular 110° C.-120° C., particularly preferably 115° C.-120° C. and under a pressure of from 1 to 25 mbar, preferably 1 to 15 mbar and particularly preferably 1-10 mbar. The esterification reaction i-3) is continued until the content of alkyl esters b2) and/or b1) has fallen to at least 8 wt. %, based on the total composition, preferably at least 5 wt. %, based on the total composition. The reaction times are conventionally in the range of from 5 to 15 h and can be reduced considerably by efficient stirring.

The products produced in this way conventionally have the carbohydrate partial ester distribution described above. The proportion of unreacted glycoses in the crude product is conventionally at most 15 wt. %, preferably at most 10 wt. %.

In a further embodiment a gentle stream of nitrogen inert gas is passed through the reaction mixture, but without leaving the abovementioned pressure conditions. This procedure leads to products of lighter color.

In a process version which is preferred according to the invention the hot reaction product is dissolved in ester oil c1) and/or c2) as an emollient.

After the unreacted carbohydrates have been separated off, the mixture is bleached with hydrogen peroxide—preferably under a nitrogen atmosphere—optionally treated with an acid to establish a pH of between 6 and 8 and then optionally filtered over a filtration aid.

In one alternative no further emollients are employed during the working up.

In a further alternative further emollients are employed neither during the preparation nor during the working up.

In one version further emollients are employed during the working up.

Further emollients in the context of the invention are to be understood here as meaning oily substances which become liquid at 40° C., preferably at 60° C. and under normal pressure.

The emollients must be able to dissolve, either at room temperature or optionally under the influence of heat, the carbohydrate partial esters prepared by the process according to the invention. Oily substances which are solid, paste-like or wax-like at room temperature but in the molten state have a good dissolving power for the carbohydrate partial esters are also suitable as an emollient, that according to the invention which are suitable are, for example, hydrocarbons, ester oils, polyols, dialkyl ethers, dialkyl carbonates, such as, for example, Cetiol® S, Sylko® 365 NF, Panalane® L 14 E, Cetiol® NPC, Cetiol® SN, Cetiol® PGL1 Edenor® V, Cetiol® OE, Cetiol® CC. Hydrocarbons are preferably suitable according to the invention, and among these a polyisobutene which is liquid at 20° C. and under normal pressure, in particular a hydrogenated polyisobutene which is commercially available under the name Panalane® L14 E (manufacturer: Amoco; INCI name: hydrogenated polyisobutene). In addition to a low viscosity, the latter is distinguished by very good dissolving properties for the sucrose esters prepared according to the invention and sensorial advantages with respect to the cosmetic end formulations. Liquid, paste-like or wax-like ester oils of C6-C22-fatty acids and C1-C3-alcohols, such as e.g. Edenor® ME 16V, are also particularly suitable as solvents for carbohydrate partial esters prepared according to the invention.

In one embodiment, after the synthesis of the carbohydrate partial esters a deactivation of the catalyst is carried out neither in the further process steps nor during the working up.

The unreacted carbohydrates can be separated off, for example, by decanting, centrifuging and/or by filtration. In one embodiment of the invention the unreacted carbohydrates are separated off by decanting and/or centrifuging.

In a further embodiment a decanting centrifuge is employed, preferably in a continuous process, in particular as a distinction from screen centrifuges.

It is preferable according to the invention to carry out the separating off by decanting.

It is essential for the process according to the invention that the product from step i) has the same carbohydrate partial ester distribution as one of the products from step iii), iv) or v).

The intermediate, that is to say the product from step i), is viscous, cloudy and dark brown.

After the separating off compositions in which the residual sugar content is less than 10 wt. %, in particular less than 5 wt. %, based on the total composition of the product mixture, are conventionally obtained.

A bleaching step with hydrogen peroxide, which is preferably carried out under a nitrogen atmosphere, then takes place. The reaction product is then dried again in vacuo in order to remove residual amounts of water.

The pH of the product mixture should be between 6 and 8 and is optionally adjusted by addition of acid. The conventional mineral acids or fruit acids can be employed for this. The addition of citric acid or lactic acid is particularly suitable according to the invention. Lactic acid is particularly suitable since the products neutralized in this way lead to more stable cosmetic end formulations.

Carbohydrate partial esters are prepared with the process according to the invention in the same production time as in the process of EP 1 811 951 B1. The carbohydrate partial ester distribution of the crude product is identical to that of the end product.

The present invention also provides a composition prepared in a process as described above, preferably characterized by the following steps:
i) esterification of a carbohydrate with an alkyl ester b) in the presence of a catalyst,
ii) addition of ester oils c),
iii) separating off of the crude product from the residual sugar, optionally
iv) bleaching of the liquid phase separated off and optionally
v) production of a shaped body.

The invention also provides cosmetic and/or pharmaceutical products or foodstuffs containing a composition according to the invention or a shaped body or a product produced in a process according to the invention.

Cosmetic and/or pharmaceutical products in the context of the invention are: hair shampoos, hair lotions, foam baths, shower baths, creams, gels, lotions, alcoholic and aqueous/alcoholic solutions, emulsions, wax/fat compositions, stick preparations, powders or ointments serve.

These compositions can furthermore contain as further auxiliary substances and additives mild surfactants, oily substances, emulsifiers, pearlescent waxes, agents which impart consistency, thickening agents, super-oiling agents, stabilizers, polymers, silicone compounds, fats, waxes, lecithins, phospholipids, biogenic active compounds, UV light protection factors, antioxidants, deodorants, antiperspirants, antidandruff agents, film-forming agents, swelling agents, insect repellants, self-tanning agents, tyrosine inhibitors (depigmentation agents), hydrotropic substances, solubilizers, preservatives, perfume oils, dyestuffs, pigments, substances and/or pigments having color-imparting properties, bactericides or bacteriostatic active compounds, perspiration-absorbing substances and the like.

Surfactants:

The compositions can contain as surface-active substances anionic, nonionic, cationic and/or amphoteric or zwitterionic surfactants, the proportion of which in the compositions is conventionally about 1 to 70, preferably 5 to 50 and in particular 10 to 30 wt. %. Typical examples of anionic surfactants soaps, alkylbenzenesulfonates, alkanesulfonates, olefinsulfonates, alkyl ether-sulfonates, glycerol ether-sulfonates, alpha-methyl ester-sulfonates, sulfo-fatty acids, alkyl sulfates, fatty alcohol ether-sulfates, glycerol ether-sulfates, fatty acid ether-sulfates, hydroxy-mixed ether-sulfates, monoglyceride (ether)sulfates, fatty acid amide (ether)sulfates, mono- and dialkyl sulfosuccinates, mono- and dialkyl sulfosuccinamates, sulfotriglycerides, amide soaps, ether-carboxylic acids and salts thereof, fatty acid isethionates, fatty acid sarcosinates, fatty acid taurides, N-acylamino acids, such as, for example, acyl lactylates, acyl tartrates, acyl glutamates and acyl aspartates, alkyl oligoglucoside-sulfates, protein-fatty acid condensates (in particular plant products based on wheat) and alkyl (ether) phosphates. If the anionic surfactants contain polyglycol ether chains, these can have a conventional, but preferably a narrowed distribution of homologues. Typical examples of nonionic surfactants are fatty alcohol polyglycol ethers, alkylphenol polyglycol ethers, fatty acid polyglycol esters, fatty acid amide polyglycol ethers, fatty amine polyglycol ethers, alkoxylated triglycerides, mixed ethers or mixed formals, optionally partially oxidized alk(en)yl oligoglycosides and glucuronic acid derivatives, fatty acid N-alkylglucamides, protein hydrolysates (in particular plant products based on wheat), polyol fatty acid esters, sugar esters, sorbitan esters, polysorbates and amine oxides. If the nonionic surfactants contain polyglycol ether chains, these can have a conventional, but preferably a narrowed distribution of homologues. Typical examples of cationic surfactants are quaternary ammonium compounds, such as, for example, dimethyldistearylammonium chloride, and ester-quats, in particular quaternized fatty acid trialkanolamine ester salts. Typical examples of amphoteric or zwitterionic surfactants are alkylbetaines, alkylamidobetaines, aminopropionates, aminoglycinates, imidazoliniumbetaines and sulfobetaines. The surfactants mentioned are exclusively known compounds. With respect to the structure and preparation of these substances, reference may be made to relevant overview works, for example J.Falbe (ed.), "Surfactants in Consumer Products", Springer Verlag, Berlin, 1987, p. 54-124 or J.Falbe (ed.), "Katalysatoren, Tenside and Mineraloladditive", Thieme Verlag, Stuttgart, 1978, p. 123-217. Typical examples of particularly suitable mild surfactants, i.e. surfactants which are particularly tolerated by skin, are fatty alcohol polyglycol ether-sulfates, monoglyceride sulfates, mono- and/or dialkyl sulfosuccinates, fatty acid isethionates, fatty acid sarcosinates, fatty acid taurides, fatty acid glutamates, olefin-sulfonates, ether-carboxylic acids, alkyl oligoglucosides, fatty acid glucamides, alkylamidobetaines, amphoacetals and/or protein-fatty acid condensates, the latter preferably based on wheat proteins or salts thereof.

Oily Substances:

Body care compositions, such as creams, lotions and milks, conventionally contain a number of further oily substances and emollients which contribute towards further optimization of the sensorial properties. Depending on the nature of the formulation, the oily substances can be contained in this in a total amount of from 1 to 90 wt. %, in particular in a total amount of 1-50 wt. %, preferably 5-25 wt. % and in particular 5-15 wt. %.

Substances which come as oily substances are, for example, Guerbet alcohols based on fatty alcohols having 6 to 18, preferably 8 to 10 carbon atoms, esters of linear $C_6$-$C_{22}$-fatty acids with linear or branched $C_6$-$C_{22}$-fatty alcohols and esters of branched $C_6$-$C_{13}$-carboxylic acids with linear or branched $C_6$-$C_{22}$-fatty alcohols, such as e.g. myristyl myristate, myristyl palmitate, myristyl stearate, myristyl isostearate, myristyl oleate, myristyl behenate, myristyl erucate, cetyl myristate, cetyl palmitate, cetyl stearate, cetyl isostearate, cetyl oleate, cetyl behenate, cetyl erucate, stearyl myristate, stearyl palmitate, stearyl stearate, stearyl isostearate, stearyl oleate, stearyl behenate, stearyl erucate, isostearyl myristate, isostearyl palmitate, isostearyl stearate, isostearyl isostearate, isostearyl oleate, isostearyl behenate, isostearyl oleate, oleyl myristate, oleyl palmitate, oleyl stearate, oleyl isostearate, oleyl oleate, oleyl behenate, oleyl erucate, behenyl myristate, behenyl palmitate, behenyl stearate, behenyl isostearate, behenyl oleate, behenyl behenate, behenyl erucate, erucyl myristate, erucyl palmitate, erucyl stearate, erucyl isostearate, erucyl oleate, erucyl behenate and erucyl erucate. In addition, esters of linear $C_6$-$C_{22}$-fatty acids with branched alcohols, in particular 2-ethylhexanol, esters of $C_{18}$-$C_{38}$-alkyl hydroxycarboxylic acids with linear or branched $C_6$-$C_{22}$-fatty alcohols (cf. DE 19756377 a2), in particular dioctyl malate, esters of linear and/or branched fatty acids with polyhydric alcohols (such as e.g. propylene glycol, dimer diol or trimer triol) and/or Guerbet alcohols, triglycerides based on $C_6$-$C_{10}$-fatty acids, liquid mono/di/triglyceride mixtures based on $C_6$-$C_{18}$-fatty acids, esters of $C_6$-$C_{22}$-fatty alcohols and/or Guerbet alcohols with aromatic carboxylic acids, in particular benzoic acid, esters of $C_2$-$C_{12}$-dicarboxylic acids with linear or branched alcohols having 1 to 22 carbon atoms or polyols having 2 to 10 carbon atoms and 2 to 6 hydroxyl groups, plant oils, branched primary alcohols, substituted cyclohexanes, linear and branched $C_6$-$C_{22}$-fatty alcohol carbonates, such as e.g. Dicaprylyl Carbonate (Cetiol® OE), Guerbet carbonates based on fatty alcohols having 6 to 18, preferably 8 to 10 C atoms, esters of benzoic acid with linear and/or branched $C_6$-$C_{22}$-alcohols (e.g. Finsolv$\Sigma$ TN), linear or branched, symmetric or unsymmetric dialkyl ethers having 6 to 22 carbon atoms per alkyl group, such as e.g. Dicaprylyl Ether (Cetiol® OE), ring-opening products of epoxidized fatty acid esters with polyols, silicone oils (cyclomethicone, silicon methicone types and others) and/or aliphatic or naphthenic hydrocarbons, such as e.g. squalane, squalene or dialkylcyclohexanes are suitable in consideration.

Emulsifiers:

Possible emulsifiers are, for example, nonionic surfactants from at least one of the following groups:

alkyl and/or alkenyl oligoglycosides having 8 to 22 carbon atoms in the alk(en)yl radical and ethoxylated analogues thereof;

partial esters of glycerol and/or sorbitan with unsaturated, linear or saturated, branched fatty acids having 12 to 22 carbon atoms and/or hydroxycarboxylic acids having 3 to 18 carbon atoms and adducts thereof with 1 to 30 mol of ethylene oxide;

partial esters of polyglycerol (average degree of self-condensation 2 to 8), polyethylene glycol (molecular weight 400 to 5,000), trimethylolpropane, pentaerythritol, sugar alcohols, e.g. sorbitol, alkyl glucosides (e.g. methyl glucoside, butyl glucoside, lauryl glucoside) and polyglucosides (e.g. cellulose) with saturated and/or unsaturated, linear or branched fatty acids having 12 to 22 carbon atoms and/or hydroxycarboxylic acid having 3 to 18 carbon atoms and adducts thereof with 1 to 30 mol of ethylene oxide;

mixed esters of pentaerythritol, fatty acids, citric acid and fatty alcohol according to DE 1165574 PS and/or mixed esters of fatty acids having 6 to 22 carbon atoms, methylglucose and polyols, preferably glycerol or polyglycerol;

block copolymers, e.g. Polyethylene Glycol 30 Dipolyhydroxystearate;

polymeric emulsifiers, e.g. Pemulen types (TR-1, TR-2) from Goodrich and glycerol carbonate.

Polyglycerol Esters:

Typical examples of suitable polyglycerol esters are Polyglyceryl-2 Dipolyhydroxystearate (Dehymuls$\Sigma$ PGPH), Polyglycerol-3 Diisostearate (Lameform$\Sigma$ TGI), Polyglyceryl-4 Isostearate (Isolan$\Sigma$ GI 34), Polyglyceryl-3 Oleate, Diisostearoyl Polyglyceryl-3 Diisostearate (Isolan$\Sigma$ PDI), Polyglyceryl-3 Methylglucose Distearate (Tego Care$\Sigma$ 450), Polyglyceryl-3 Beeswax (Cera Bellina$\Sigma$), Polyglyceryl-4 Caprate (Polyglycerol Caprate T2010/90), Polyglyceryl-3 Cetyl Ether (Chimexane$\Sigma$ NL), Polyglyceryl-3 Distearate (Cremophor$\Sigma$ GS 32) and Polyglyceryl Polyricinoleate (Admul$\Sigma$ WOL 1403), Polyglyceryl Dimerate Isostearate and mixtures thereof. Examples of further suitable polyol esters are the mono-, di- and triesters, optionally reacted with 1 to 30 mol of ethylene oxide, of trimethylolpropane or pentaerythritol with lauric acid, coconut fatty acid, tallow fatty acid, palmitic acid, stearic acid, oleic acid, behenic acid and the like.

Anionic Emulsifiers:

Typical anionic emulsifiers are aliphatic fatty acids having 12 to 22 carbon atoms, such as, for example, palmitic acid, stearic acid or behenic acid, and dicarboxylic acids having 12 to 22 carbon atoms, such as, for example, azelaic acid or sebacic acid.

Amphoteric and Cationic Emulsifiers:

Zwitterionic surfactants can furthermore be used as emulsifiers. Those surface-active compounds which carry at least one quaternary ammonium group and at least one carboxylate and one sulfonate group in the molecule are called zwitterionic surfactants. Particularly suitable zwitterionic surfactants are the so-called betaines, such as the N-alkyl-N,N-dimethylammonium glycinates, for example coco-alkyldimethylammonium glycinate, N-acylaminopropyl-N, N-dimethylammonium glycinates, for example coco-acylamimopropyldimethylammonium glycinate, and 2-alkyl-3-carboxymethyl-3-hydroxyethylimidazolines having in each case 8 to 18 C atoms in the alkyl or acyl group and coco-acylaminoethylhydroxyethylcarboxymethyl glycinate. The fatty acid amide derivative known under the CTFA name Cocamidopropyl Betaine is particularly preferred. Ampholytic surfactants are likewise suitable emulsifiers. Ampholytic surfactants are understood as meaning those surface-active compounds which contain, apart from a $C_{8/18}$-alkyl or acyl group, at least one free amino group and at least one COOH or —$SO_3H$ group in the molecule and are capable of formation of inner salts. Examples of suitable ampholytic surfactants are N-alkylglycines, N-alkylpropionic acids, N-alkylaminobutyric acids, N-alkyliminodipropionic acids, N-hydroxyethyl-N-alkylamidopropylglycines, N-alkyltaurines, N-alkylsarcosines, 2-alkylaminopropionic acids and alkylaminoacetic acids having in each case about 8 to 18 C atoms in the alkyl group. Particularly preferred ampholytic surfactants are N-coco-alkylaminopropionate, coco-acylaminoethylaminopropionate and $C_{12/18}$-acylsarcosine. Finally, cationic surfactants are also possible emulsifiers, those of the ester-quat type, preferably methyl-quaternized di-fatty acid triethanolamine ester salts, being particularly preferred.

Fats and Waxes:

Fats and waxes are added to the body care products as care substances and also in order to increase the consistency of the cosmetics. Typical examples of fats are glycerides, i.e. solid plant or animal products, which substantially consist of mixed glycerol esters of higher fatty acids. Fatty acid partial glycerides, i.e. technical grade mono- and/or diesters of glycerol with fatty acids having 12 to 18 carbon atoms, such as, for example, glycerol mono/dilaurate, -palmitate or -stearate, are also possible for this. Typical examples of fats are glycerides, i.e. solid or liquid plant or animal products, which substantially consist of mixed glycerol esters of higher fatty acids, possible waxes are, inter alia, natural waxes, such as e.g. candelilla wax, carnauba wax, Japan wax, esparto grass wax, cork wax, guaruma wax, rice germ oil wax, sugar cane wax, ouricury wax, montan wax, beeswax, shellac wax, spermaceti, lanolin (wool wax), uropygium fat, ceresin, ozocerite (earth wax), petrolatum, paraffin waxes, microwaxes; chemically modified waxes (hard waxes), such as e.g. montan ester waxes, Sasol waxes, hydrogenated jojoba waxes and synthetic waxes, such as e.g. polyalkylene waxes and polyethylene glycol waxes. In addition to the fats, fat-like substances, such as lecithins and phospholipids, are also possible as additives. The designation lecithins is understood by the person skilled in the art as meaning those glycero-phospholipids which form from fatty acids, glycerol, phosphoric acid and choline by esterification. Lecithin are therefore also as phosphatidylcholines (PC) in technical circles. Example of natural lecithins which may be mentioned are the cephalins, which are also called phosphatidic acids and are derivatives of 1,2-diacyl-sn-glycerol-3-phosphoric acids. In contrast, phospholipids are usually understood as meaning mono- and preferably diesters of phosphoric acid with glycerol (glycerol phosphates), which are generally counted among the fats. In addition, sphingosines and sphingolipids are also possible.

Pearlescent Waxes:

Possible pearlescent waxes are, for example: alkylene glycol esters, specifically ethylene glycol distearate; fatty acid alkanolamides, specifically coconut fatty acid diethanolamide; partial glycerides, specifically stearic acid monoglyceride; esters of polybasic, optionally hydroxy-substituted carboxylic acids with fatty alcohols having 6 to 22 carbon atoms, specifically long-chain esters of tartaric acid; fatty substances, such as, for example, fatty alcohols, fatty ketones, fatty aldehydes, fatty ethers and fatty carbonates, which contain at least 24 carbon atoms in total, specifically laurone and distearyl ether; fatty acids, such as stearic acid, hydroxystearic acid or behenic acid, ring-opening products of olefin epoxides having 12 to 22 carbon atoms with fatty alcohols having 12 to 22 carbon atoms and/or polyols having 2 to 15 carbon atoms and 2 to 10 hydroxyl groups and mixtures thereof.

Agents which Impart Consistency and Thickening Agents:

Possible agents which impart consistency are primarily fatty alcohols or hydroxy-fatty alcohols having 12 to 22 and preferably 16 to 18 carbon atoms and in addition partial glycerides, fatty acids or hydroxy-fatty acids. A combination of these substances with alkyl oligoglucosides and/or fatty acid N-methylglucamides of the same chain length and/or polyglycerol poly-12-hydroxystearates is preferred. Suitable thickening agents are, for example, Aerosil types (hydrophilic silicas), polysaccharides, in particular xanthan gum, guar-guar, agar-agar, alginates and tyloses, carboxymethylcellulose and hydroxyethyl- and hydroxypropylcellulose, furthermore higher molecular weight polyethylene glycol mono- and diesters of fatty acids, polyacrylates (e.g. CarbopolsΣ and Pemulen types from Goodrich; SynthalensΣ from Sigma; Keltrol types from Kelco; Sepigel types from Seppic; Salcare types from Allied Colloids), polyacrylamides, polymers, polyvinyl alcohol and polyvinylpyrrolidone. Bentonites, such as e.g. Bentone® Gel VS-5PC (Rheox), which is a mixture of cyclopentasiloxane, Disteardimonium Hectorite and propylene carbonate, have also proved to be particularly effective. Surfactants such as, for example, ethoxylated fatty acid glycerides, esters of fatty acids with polyols, such as, for example, pentaerythritol or trimethylolpropane, fatty alcohol ethoxylates with a narrowed homologue distribution or alkyl oligoglucosides and electrolytes, such as sodium chloride and ammonium chloride, are furthermore possible.

Super-Oiling Agents:

Super-oiling agents which can be used are substances such as, for example, lanolin and lecithin and polyethoxylated or acylated lanolin and lecithin derivatives, polyol fatty acid esters, monoglycerides and fatty acid alkanolamides, the latter simultaneously serving as foam stabilizers.

Stabilizers:

Stabilizers which can be employed are metal salts of fatty acids, such as e.g. magnesium, aluminum and/or zinc stearate or ricinoleate.

Polymers:

Suitable cationic polymers are, for example, cationic cellulose derivatives, such as e.g. a quaternized hydroxyethylcellulose which is obtainable from Amerchol under the name Polymer JR 400Σ, cationic starch, copolymers of diallylammonium salts and acrylamides, quaternized vinylpyrrolidone/vinylimidazole polymers, such as e.g. Luviquat∑ (BASF), condensation products of polyglycols and amines, quaternized collagen polypeptides, such as, for example, Lauryldimonium Hydroxypropyl Hydrolyzed Collagen (Lamequat∑ L/Grünau), quaternized wheat polypeptides, polyethylenimine, cationic silicone polymers, such as e.g. amodimethicone, copolymers of adipic acid and dimethylaminohydroxypropyldiethylenetriamine (Cartaretine∑/Sandoz), copolymers of acrylic acid with dimethyldiallylammonium chloride (Merquat∑ 550/Chemviron, polyaminopolyamides, as described e.g., in FR 2252840 A, and crosslinked water-soluble polymers thereof, cationic chitin derivatives, such as, for example, quaternized chitosan, condensation products, optionally distributed in microcrystalline form, of dihaloalkyls, such as e.g. dibromobutane with bisdialkylamines, such as e.g. bis-dimethylamino-1,3-propane, cationic guar gum, such as e.g. Jaguar∑ CBS, Jaguar∑ C-17, Jaguar∑ C-16 from Celanese, quaternized ammonium salt polymers, such as e.g. Mirapol∑ A-15, Mirapol∑AD-1, Mirapol∑ AZ-1 from Miranol.

Possible anionic, zwitterionic, amphoteric and nonionic polymers are, for example, vinyl acetate/crotonic acid copolymers, vinylpyrrolidone/vinyl acrylate copolymers, vinyl acetate/butyl maleate/isobornyl acrylate copolymers, methyl vinyl ether/maleic anhydride copolymers and esters thereof, non-crosslinked and polyol-crosslinked polyacrylic acids, acrylamidopropyltrimethylammonium chloride/acrylate copolymers, octylacrylamide/methyl methacrylate/tert-butylaminoethyl methacrylate/2-hydroxypropyl methacrylate copolymers, polyvinylpyrrolidone, vinylpyrrolidone/vinyl acetate copolymers, vinylpyrrolidone/dimethylaminoethyl methacrylate/vinylcaprolactam terpolymers and optionally derivatized cellulose ethers and silicones. Further suitable polymers and thickening agents are listed in Cosm. Toil. 108, 95 (1993).

Silicone Compounds:

Suitable silicone compounds are, for example, dimethylpolysiloxanes, methylphenylpolysiloxanes, cyclic silicones and amino-, fatty acid-, alcohol-, polyether-, epoxy-, fluorine-, glycoside- and/or alkyl-modified silicone compounds, which can be either liquid or resinous at room temperature. Simethicones, which are mixtures of dimethicones having an average chain length of from 200 to 300 dimethylsiloxane units and hydrogenated silicates, are furthermore suitable. A detailed overview of suitable volatile silicones is moreover to be found by Todd et al. in Cosm. Toil. 91, 27 (1976).

UV Light Protection Filters and Antioxidants:

UV light protection factors are to be understood as meaning, for example, organic substances which are liquid or crystalline at room temperature (light protection filters) and which are capable of absorbing ultraviolet rays and of releasing the energy absorbed again in the form of longer-wavelength radiation, e.g. heat. UVB filters can be oil-soluble or water-soluble.

Oil-soluble substances which are to be mentioned are e.g.:
3-benzylidenecamphor and 3-benzylidenenorcamphor (Mexoryl SDS 20) derivatives thereof, e.g. 3-(4-methylbenzylidene)camphor as described in EP 0693471 B1;
3-(4'-trimethylammonium)-benzylidenebornan-2-one methyl-sulfate (Mexoryl SO)
3,3'-(1,4-phenylenedimethine)-bis(7,7-dimethyl-2-oxobicyclo[2.2.1]heptane-1-methanesulfonic acid) and salts (Mexoryl SX)
3-(4'-sulfo)-benzylidenebornan-2-one and salts (Mexoryl SL)
polymer of N-{(2 and 4)-[2-oxoborn-3-ylidene) methyl}benzyl]acrylamide (Mexoryl SW)
2-(2H-benzotriazol-2-yl)-4-methyl-6-(2-methyl-3-(1,3,3,3-tetramethyl-1-(trimethylsilyloxy)disiloxanyl)propyl) phenol (Mexoryl XL)
4-aminobenzoic acid derivatives, preferably 4-(dimethylamino)benzoic acid 2-ethyl hexyl-ester, 4-(dimethylamino)benzoic acid 2-octyl ester and 4-(dimethylamino)benzoic acid amyl ester;
esters of cinnamic acid, preferably 4-methoxycinnamic acid 2-ethylhexyl ester, 4-methoxycinnamic acid propyl ester, 4-methoxycinnamic acid isoamyl ester, 2-cyano-3,3-phenylcinnamic acid 2-ethylhexyl ester (octocrylene);
esters of salicylic acid, preferably salicylic acid 2-ethylhexyl ester, salicylic acid 4-isopropylbenzyl ester, salicylic acid homomenthyl ester;
derivatives of benzophenone, preferably 2-hydroxy-4-methoxybenzophenone, 2-hydroxy-4-methoxy-4'-methylbenzophenone, 2,2'-dihydroxy-4-methoxybenzophenone;
esters of benzalmalonic acid, preferably 4-methoxybenzalmalonic acid di-2-ethylhexyl ester;
triazine derivatives, such as e.g. 2,4,6-trianilino-(p-carbo-2'-ethyl-1'-hexyloxy)-1,3,5-triazine and 2,4,6-tris[p-(2-ethylhexyloxycarbonyl)anilino]-1,3,5-triazine (Uvinul T 150) as described in EP 0818450 A1 or 4,4'-[(6-[4-((1,1-dimethylethyl)aminocarbonyl)phenylamino]-1,3,5-triazine-2,4-diyl)diimino]-bis(benzoic acid 2-ethylhexyl ester) (Uvasorb∑ HEB);
2,2(-methylene-bis(6-(2H-benzotriazol-2-yl)-4-(1,1,3,3-tetramethylbutyl)phenol) (Tinosorb M);
2,4-bis[4-(2-ethylhexyloxy)-2-hydroxyphenyl]-6-(4-methoxyphenyl)-1,3,5-triazine (Tinosorb S);
propane-1,3-diones, such as e.g. 1-(4-tert-butylphenyl)-3-(4'-methoxyphenyl)propane-1,3-dione;
ketotricyclo(5.2.1.0)decane derivatives, as described in EP 0694521 B1;
dimethicodiethylbenzalmalonate (Parsol SLX).

Possible water-soluble UV filters are:
2-phenylbenzimidazole-5-sulfonic acid and alkali metal, alkaline earth metal, ammonium, alkylammonium, alkanolammonium and glucammonium salts thereof;
2,2(-(1,4-phenylene)bis(1H-benzimidazole-4,6-disulfonic acid, monosodium salt) (Neo Heliopan AP)
sulfonic acid derivatives of benzophenones, preferably 2-hydroxy-4-methoxybenzophenone-5-sulfonic acid and its salts;
sulfonic acid derivatives of 3-benzylidenecamphor, such as e.g. 4-(2-oxo-3-bornylidene-methyl)benzenesulfonic acid and 2-methyl-5-(2-oxo-3-bornylidene)sulfonic acid and salts thereof.

Possible typical UV-A filters are, in particular, derivatives of benzoylmethane, such as, for example, 1-(4'-tert-butylphenyl)-3-(4'-methoxyphenyl)propane-1,3-dione, 4-tert-butyl-4'-methoxydibenzoylmethane (Parsol∑ 1789), 1-phenyl-3-(4'-isopropylphenyl)propane-1,3-dione and enamine compounds, as described in DE 19712033 A1 (BASF) and Benzoic Acid 2-[4-(Diethylamino)-2-Hydroxybenzoyl]-, Hexyl Ester (Uvinul∑ A plus).

The UV-A and UV-B filters can of course also be employed in mixtures. Particularly favorable combinations consist of the derivatives of benzoylmethane, e.g. 4-tert-butyl-4'-methoxydibenzoylmethane (ParsolE 1789), and 2-cyano-3,3-phenylcinnamic acid 2-ethylhexyl ester (octocrylene) in combination with esters of cinnamic acid, preferably 4-methoxycinnamic acid 2-ethylhexyl ester and/or 4-methoxycinnamic acid propyl ester and/or 4-methoxycinnamic acid isoamyl ester. Such combinations are advantageously combined with water-soluble filters, such as e.g. 2-phenylbenzimidazole-5-sulfonic acid and alkali metal, alkaline earth metal, ammonium, alkylammonium, alkanolammonium and glucammonium salts thereof.

UV light protection filters which are preferred according to the invention are selected from Appendix VII of the European cosmetics legislation (24th Adapting Commission Directive, 29th February 2000).

In addition to the soluble substances mentioned, insoluble light protection pigments, namely finely disperse metal oxides or salts, are also possible for this purpose. Examples of suitable metal oxides are, in particular, zinc oxide and titanium dioxide, and in addition oxides of iron, zirconium, silicon, manganese, aluminum and cerium and mixtures thereof. Salts which can be employed are silicates (talc), barium sulfate or zinc stearate. The oxides and salts are used in the form of the pigments for skin care and skin protection emulsions and also for decorative cosmetics. The particles should have an average diameter of less than 100 nm, preferably between 5 and 50 nm and in particular between 15 and 30 nm. They can have a spherical shape, but those particles which have an ellipsoid shape or a shape which deviates otherwise from the spherical form can also be employed. The pigments can also present in a surface-treated form, i.e. hydrophilized or hydrophobized. Typical examples are coated titanium dioxides, such as e.g. titanium dioxide T 805 (Degussa) or Eusolex® T, Eusolex® T-2000, Eusolex® T-Aqua, Eusolex® AVO, Eusolex® T-ECO Eusolex® T-OLEO and Eusolex® T-S (Merck). Typical examples of are zinc oxides, such as e.g. Zinc Oxide neutral, Zinc Oxide NDM (Symrise) or Z-Cote® (BASF) or SUN-ZnO-AS and SUNZnO-NAS (Sunjun Chemical Co. Ltd.). Possible hydrophobic coating agents in this context are above all silicones, and in this context specifically trialkoxyoctylsilanes or simethicone. So-called micro- or nanopigments are preferably employed in sunscreen compositions. Micronized zinc oxide is preferably used. Further suitable UV light protection filters are known from the overview by P. Finkel in SÖFW-Journal 122, 543 (1996) and Parf. Kosm. 3, 11 (1999).

In addition to the two abovementioned groups of primary light protection substances, secondary light protection agents of the antioxidant type which interrupt the photochemical reaction chain triggered when UV radiation penetrates into the skin can also be employed. Typical examples of these are amino acids (e.g. glycine, histidine, tyrosine, tryptophan) and derivatives thereof, imidazoles (e.g. urocanic acid) and derivatives thereof, peptides, such as D,L-carnosine, D-carnosine, L-carnosine and derivatives thereof (e.g. anserine), carotenoids, carotenes (e.g. -carotene, -carotene, lycopene) and derivatives thereof, chlorogenic acid and derivatives thereof, liponic acid and derivatives thereof (e.g. dihydroliponic acid), aurothioglucose, propylthiouracil and other thiols (e.g. thioredoxin, glutathione, cysteine, cystine, cystamine and glycosyl, N-acetyl, methyl, ethyl, propyl, amyl, butyl and lauryl, palmitoyl, oleyl, -linoleyl, cholesteryl and glyceryl esters thereof) as well as salts thereof, dilauryl thiodipropionate, distearyl thiodipropionate, thiodipropionic acid and derivatives thereof (esters, ethers, peptides, lipids, nucleotides, nucleosides and salts) as well as sulfoximine compounds (e.g. buthionine sulfoximine, homocysteine sulfoximine, buthionine sulfones, penta-, hexa-, heptathionine sulfoximine) in very low tolerated dosages (e.g. pmol to mol/kg), furthermore (metal) chelators, (e.g. α-hydroxy-fatty acids, palmitic acid, phytic acid, lactoferrin), α-hydroxy acids (e.g. citric acid, lactic acid, malic acid), humic acid, bile acid, bile extracts, bilirubin, biliverdin, EDTA, EGTA and derivatives thereof, unsaturated fatty acids and derivatives thereof (e.g. gamma-linolenic acid, linoleic acid, oleic acid), folic acid and derivatives thereof, ubiquinone and ubiquinol and derivatives thereof, vitamin C and derivatives (e.g. ascorbyl palmitate, Mg ascorbyl phosphate, ascorbyl acetate), tocopherols and derivatives thereof (e.g. vitamin E acetate), vitamin A and derivatives (vitamin A palmitate) as well as coniferyl benzoate of benzoin resin, rutic acid and derivatives thereof, α-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof (e.g. ZnO, ZnSO4), selenium and derivatives thereof (e.g. selenium methionine), stilbenes and derivatives thereof (e.g. stilbene oxide, trans-stilbene oxide) and the derivatives of these active compounds mentioned which are suitable according to the invention (salts, esters, ethers, sugars, nucleotides, nucleosides, pitides and lipids).

The invention thus also provides sunscreen compositions, characterized in that they contain organic UV light protection filters which are selected from the group formed by 3-benzylidenecamphor and 3-benzylidenenorcamphor and derivatives thereof, 4-aminobenzoic acid derivatives, cinnamic acid esters, salicylic acid esters, benzalmalonic acid esters, benzophenone derivatives, benzoylmethane derivatives, triazine derivatives, propane-1,3-diones, ketotricyclo (5.2.1.0)decane derivatives, 2-phenylbenzimidazole-5-sulfonic acid and salts thereof and sulfonic acid derivatives of benzophenone and of 3-benzylidenecamphor.

The sunscreen compositions according to the invention can also contain inorganic UV light protection pigments which are selected from the group formed by titanium dioxide, zinc oxide, iron oxide, aluminum oxide, cerium oxide, zirconium oxide, silicates, barium sulfate and zinc stearate.

The sunscreen compositions according to the invention can also contain antioxidants which are selected from the group formed by amino acids and derivatives thereof, imidazoles (e.g. urocanic acid) and derivatives thereof, peptides and derivatives thereof, carotenoids, carotenes and derivatives thereof, chlorogenic acids and derivatives thereof, liponic acid and derivatives thereof, aurothioglucose, propylthiouracil and other thiols and salts thereof, dilauryl thiodipropionate, distearyl thiodipropionate, thiodipropionic acid and derivatives thereof, sulfoximine compounds, (metal) chelators, alpha-hydroxy acids, humic acid, bile acid, bile extracts, bilirubin, biliverdin, EDTA, EGTA and derivatives thereof, unsaturated fatty acids and derivatives thereof, folic acid and derivatives thereof, ubiquinone, ubiquinol and derivatives thereof, vitamin C and derivatives thereof, tocopherols and derivatives thereof, vitamin A and derivatives thereof, coniferyl benzoate, rutic acid and derivatives thereof, alpha-glycosylrutin, ferulic acid, furfurylideneglucitol, carnosine, butylhydroxytoluene, butylhydroxyanisole, nordihydroguaiac resin acid, nordihydroguaiaretic acid, trihydroxybutyrophenone, uric acid and derivatives thereof, mannose and derivatives thereof, superoxide dismutase, zinc and derivatives thereof, selenium and derivatives thereof and stilbenes and derivatives thereof.

Biogenic Active Compounds:

Biogenic active compounds are to be understood as meaning, for example, tocopherol, tocopherol acetate, tocopherol palmitate, ascorbic acid, (deoxy)ribonucleic acid and fragmentation products thereof, β-glucans, retinol, bisabolol, allantoin, phytantriol, panthenol, AHA acids, amino acids, ceramides, pseudoceramides, essential oils, plant extracts, such as e.g. Prunus extract, Bambara nut extract and vitamin complexes.

Deodorants and Germ-Inhibiting Agents:

Cosmetic deodorants counteract body odors, mask or eliminate them. Body odors are formed by the action of skin bacteria on apocrine perspiration, unpleasantly smelling degradation products being formed. Deodorants accordingly contain active compounds which function as germ-inhibiting agents, enzyme inhibitors, odor absorbers or odor maskers.

Germ-Inhibiting Agents:

Suitable germ-inhibiting agents are in principle all substances which are active against Gram-position bacteria, such as e.g. 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylene-bis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial odoriferous substances, thymol, thyme oil, eugenol, clove oil, menthol, mint oil, farnesol, phenoxyethanol, glycerol monocaprate, glycerol monocaprylate, glycerol monolaurate (GM L), diglycerol monocaprate (DMC), salicylic acid N-alkylamides, such as e.g. salicylic acid n-octylamide or salicylic acid n-decylamide.

Enzyme Inhibitors:

When perspiration is present in the armpit region, bacteria form extracellular enzymes—esterases, preferably proteases and/or lipases—which split esters contained in the perspiration and thereby release odor substances. Suitable enzyme inhibitors are, for example, esterase inhibitors. These are preferably trialkyl citrates, such as trimethyl citrate, tripropyl citrate, triisopropyl citrate, tributyl citrate and in particular triethyl citrate (Hydagen∑ CAT). The substances inhibit the enzyme activity and thereby reduce odor formation. Further substances which are possible as esterase inhibitors are sterol sulfates or phosphates, such as, for example, lanosterol, cholesterol, campesterol, stigmasterol and sitosterol sulfate and phosphate; dicarboxylic acids and esters thereof, such as, for example, glutaric acid, glutaric acid monoethyl ester, glutaric acid diethyl ester, adipic acid, adipic acid monoethyl ester, adipic acid diethyl ester, malonic acid and malonic acid diethyl ester; and hydroxy-carboxylic acids and esters thereof, such as, for example, citric acid, malic acid, tartaric acid or tartaric acid diethyl ester, and zinc glycinate.

Odor Absorbers:

Suitable odor absorbers are substances which can absorb and largely hold odor-forming compounds. They lower the partial pressure of the individual components and in this way also reduce the speed in which they spread. It is important that perfumes must remain unaffected in this context. Odor absorbers have no activity against bacteria. They contain, for example, as the main constituent a complex zinc salt of ricinoleic acid or specific fragrances of largely neutral smell which are known to the person skilled in the art as "fixatives", such as e.g. extracts of labdanum or Styrax or certain abietic acid derivatives. Odoriferous substances or perfume oils which function as odor maskers are those which in addition to their function as odor maskers impart their particular fragrance note to the deodorants. Perfume oils which may be mentioned are, for example, mixtures of natural and synthetic odoriferous substances. Natural odoriferous substances are extracts from blossom, stems and leaves, fruit, fruit pericarp, roots, wood, herbs and grasses, needles and branches, as well as resins and balsams. Animal raw materials are furthermore possible, such as, for example, civet and castoreum. Typical synthetic odoriferous compounds are products of the ester, ether, aldehyde, ketone, alcohol and hydrocarbon type. Odoriferous compounds of the ester type are e.g. benzyl acetate, p-tert-butylcyclohexyl acetate, linalyl acetate, phenylethyl acetate, linalyl benzoate, benzyl formate, allyl cyclohexylpropionate, styrallyl propionate and benzyl salicylate. The ethers include, for example, benzyl ethyl ether, the aldehydes include e.g. the linear alkanals having 8 to 18 carbon atoms, citral, citronellal, citronellyloxyacetaldehyde, cyclamenaldehyde, hydroxy-citronellal, lilial and bourgeonal, the ketones include e.g. the ionones and methyl cedryl ketone, the alcohols include anethole, citronellol, eugenol, isoeugenol, geraniol, linalool, phenylethyl alcohol and terpineol, the hydrocarbons include chiefly the terpenes and balsams. Preferably, however, mixtures of various odoriferous substances which together generate a pleasant fragrance note are used. Essential oils of relatively low volatility, which are usually used as aroma components, are also suitable as perfume oils, e.g. sage oil, chamomile oil, clove oil, Melissa oil, mint oil, cinnamon leaf oil, linden blossom oil, juniper berry oil, vetiver oil, frankincense oil, galbanum oil, labdanum oil and lavandin oil. Bergamot oil, dihydromyrcenol, lilial, lyral, citronellol, phenylethyl alcohol, alpha-hexylcinnamaldehyde, geraniol, benzylacetone, cyclamenaldehyde, linalool, Boisambrene Forte, ambroxan, indole, hedione, sandelice, lemon oil, mandarin oil, orange oil, allyl amylglycolate, cyclovertal, lavandin oil, clary sage oil, beta-damascone, Bourbon geranium oil, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl and floramate, by themselves or in mixtures, are preferably employed.

Antiperspirants:

Antiperspirants reduce formation of perspiration by influencing the activity of the eccrine sweat glands and thus counteract underarm wetness and body odor. Aqueous or anhydrous formulations of antiperspirants typically contain the following ingredients: astringent active compounds, oily components, nonionic emulsifiers, co-emulsifiers, agents which impart consistency, auxiliary substances, such as e.g. thickeners or complexing agents, and/or non-aqueous solvents, such as e.g. ethanol, propylene glycol and/or glycerol.

Suitable astringent antiperspirant active compounds are above all salts of aluminum, zirconium or of zinc. Such suitable active compounds having an antihydrotic action are e.g. aluminum chloride, aluminum chlorohydrate, aluminum dichlorohydrate, aluminum sesquichlorohydrate and complex compounds thereof, e.g. with propylene 1,2-glycol, aluminum hydroxyallantoinate, aluminum chloride tartrate, aluminum zirconium trichlorohydrate, aluminum zirconium tetrachlorohydrate, aluminum zirconium pentachlorohydrate and complex compounds thereof, e.g. with amino acids, such as glycine. In addition, antiperspirants can contain conventional oil-soluble and water-soluble auxiliary agents in relatively small amounts. Such oil-soluble auxiliary agents can be e.g.: antiinflammatory, skin-protecting or pleasantly smelling essential oils, synthetic skin-protecting active compounds and/or oil-soluble perfume oils.

Conventional water-soluble additives are e.g. preservatives, water-soluble fragrances, pH adjusters, e.g. butter mixtures, water-soluble thickening agents, e.g. water-soluble natural or synthetic polymers, such as e.g. xanthan gum, hydroxyethylcellulose, polyvinylpyrrolidone or high molecular weight polyethylene oxides.

Film-Forming Agents:

The usual film-forming agents are, for example, chitosan, microcrystalline chitosan, quaternized chitosan, polyvinylpyrrolidone, vinylpyrrolidone/vinyl acetate copolymers, polymers of the acrylic acid series, quaternary cellulose derivatives, collagen, hyaluronic acid and salts thereof and similar compounds.

Antidandruff Active Compounds:

Possible antidandruff active compounds are piroctone olamine (1-hydroxy-4-methyl-6-(2,4,4-trimethylpentyl)-2-(1H)-pyridinomonoethanolamine), Baypival® (climbazole), ketoconazoleΣ, (4-acetyl-1-Σ-4-[2-(2,4-dichlorophenyl)-r-2-(1H-imidazol-1-ylmethyl)-1,3-dioxylan-c-4-ylmethoxy-phenylEpiperazine, ketoconazole, elubiol, selenium disulfide, colloidal sulfur, sulfur-polyethylene glycol sorbitan monooleate, sulfur-ricinol-polyethoxylate, Sulfur Tar Distillate, salicylic acid (and in combination with hexachlorophene), Undecylenic Acid Monoethanolamide Sulfosuccinate Na Salt, LameponE UD (protein-undecylenic acid condensate), zinc pyrithione, aluminum pyrithione and magnesium pyrithione/dipyrithione magnesium sulfate.

Swelling Agents:

Montmorillonites, clay minerals, Pemulen and alkyl-modified Carbopol types (Goodrich) can serve as swelling agents for aqueous phases. Further suitable polymers and swelling agents can be found in the overview by R. Lochhead in Cosm. Toil. 108 95 (1993).

Insect Repellants:

Possible insect repellants are, for example, N,N-diethyl-m-toluamide, 1,2-pentanediol or 3Σ (N-n-butyl-N-acetylamino)propionic acid ethyl ester), which is marketed by Merck KGaA under the name Insect Repellent 3535, and butylacetylaminoproprionate.

Self-Tanning Agents and Depigmenting Agents:

Dihydroxyacetone is suitable as a self-tanning agent. Possible tyrosine inhibitors which prevent the formation of melanine and are used in depigmenting compositions are, for example, arbutin, ferulic acid, kojic acid, coumaric acid and ascorbic acid (vitamin C).

Hydrotropic Substances:

To improve the flow properties hydrotropic substances, such as, for example, ethanol, isopropyl alcohol, or polyols, can furthermore be employed. Polyols which are possible here have preferably 2 to 15 carbon atoms and at least two hydroxyl groups. The polyols can also contain further functional groups, in particular amino groups, or can be modified with nitrogen. Typical examples are glycerol;

alkylene glycols, such as, for example, ethylene glycol, diethylene glycol, propylene glycol, butylene glycol, hexylene glycol and polyethylene glycols having an average molecular weight of from 100 to 1,000 dalton;

technical grade oligoglycerol mixtures having a degree of self-condensation of from 1.5 to 10, such as, for example, technical grade diglycerol mixtures having a diglycerol content of from 40 to 50 wt. %;

methylol compounds, such as, in particular, trimethylolethane, trimethylolpropane, trimethylolbutane, pentaerythritol and dipentaerythritol;

lower alkyl glucosides, in particular those having 1 to 8 carbon atoms in the alkyl radical, such as, for example, methyl and butyl glucoside;

sugar alcohols having 5 to 12 carbon atoms, such as, for example, sorbitol or mannitol, sugars having 5 to 12 carbon atoms, such as, for example, glucose or sucrose;

amino-sugars, such as, for example, glucamine;

dialcoholamines, such as diethanolamine or 2-amino-1,3-propanediol.

Preservatives:

Suitable preservatives are, for example, phenoxyethanol, formaldehyde solution, parabens, pentanediol or sorbic acid and the silver complexes known by the name Surfacine® and the further substance classes listed in Appendix 6, part A and B of the cosmetics legislation.

Perfume Oils and Aromas:

Perfume oils which may be mentioned are mixtures of natural and synthetic odoriferous substances. Natural odoriferous substances are extracts from blossom (lily, lavender, rose, jasmine, orange-blossom, ylang-ylang), stems and leaves (geranium, patchouli, petitgrain), fruit (aniseed, coriander, caraway, juniper), fruit pericarp (bergamot, lemon, orange), roots (mace, *angelica*, celery, cardamom, costus, iris, calmus), wood (pine-, sandal-, guaiac-, cedar-, rosewood), herbs and grasses (tarragon, lemongrass, sage, thyme), needles and branches (spruce, fir, pine, dwarf pine), resins and balsams (*galbanum*, elemi, benzoin, myrrh, frankincense, opoponax). Animal raw materials are furthermore possible, such as, for example, civet and castoreum. Typical synthetic odoriferous compounds are products of the ester, ether, aldehyde, ketone, alcohol and hydrocarbon type. Odoriferous compounds of the ester types are e.g. benzyl acetate, phenoxyethyl isobutyrate, p-tert-butylcyclohexyl acetate, linalyl acetate, dimethylbenzylcarbinyl acetate, phenylethyl acetate, linalyl benzoate, benzyl formate, ethyl methylphenylglycinate, allyl cyclohexylpropionate, styrallyl propionate and benzyl salicylate. The ethers include, for example, benzyl ethyl ether, the aldehydes include e.g. the linear alkanals having 8 to 18 carbon atoms, citral, citronellal, citronellyloxyacetaldehyde, cyclamenaldehyde, hydroxycitronellal, lilial and bourgeonal, the ketones include e.g. the ionones, °-isomethylionone and methyl cedryl ketone, the alcohols include anethole, citronellol, eugenol, isoeugenol, geraniol, linalool, phenylethyl alcohol and terpineol, the hydrocarbons include chiefly the terpenes and balsams. Preferably, however, mixtures of various odoriferous substances which together generate a pleasant fragrance note are used. Essential oils of relatively low volatility, which are usually used as aroma components, are also suitable as perfume oils, e.g. sage oil, chamomile oil, clove oil, Melissa oil, mint oil, cinnamon leaf oil, linden blossom oil, juniper berry oil, vetiver oil, frankincense oil, galbanum oil, labolanum oil and lavandin oil. Bergamot oil, dihydromyrcenol, lilial, lyral, citronellol, phenylethyl alcohol, alpha-hexylcinnamaldehyde, geraniol, benzylacetone, cyclamenaldehyde, linalool, Boisambrene Forte, ambroxan, indole, hedione, sandelice, lemon oil, mandarin oil, orange oil, allyl amylglycolate, cyclovertal, lavandin oil, clary sage oil, beta-damascone, Bourbon geranium oil, cyclohexyl salicylate, Vertofix Coeur, Iso-E-Super, Fixolide NP, evernyl, iraldein gamma, phenylacetic acid, geranyl acetate, benzyl acetate, rose oxide, romillate, irotyl and floramate, by themselves or in mixtures, are preferably employed.

Possible aromas are, for example, peppermint oil, spearmint oil, aniseed oil, star aniseed oil, caraway oil, eucalyptus oil, fennel oil, lemon oil, wintergreen oil, clove oil, menthol and the like.

Dyestuffs:

Dyestuffs which can be used are the substances which are suitable and approved for cosmetic purposes, such as are summarized, for example, in the publication "Kosmetische Farbemittel" of the Dyestuffs Commission of the Deutsche Forschungsgemeinschaft, Verlag Chemie, Weinheim, 1984, p. 81-106. Examples are cochineal red A (C.I. 16255), patent blue V (C.I.42051), indigotine (C.I.73015), chlorophyllin (C.I.75810), quinoline yellow (C.I.47005), titanium dioxide (C.I.77891), indanthrene blue RS (C.I. 69800) and madder lake (C.I.58000). The compositions can also contain luminol as a luminescent dyestuff. These dyestuffs are conventionally employed in concentrations of from 0.001 to 0.1 wt. %, based on the total mixture.

Bactericidal and Bacteriostatic Active Compounds:

Typical examples of suitable bactericidal and bacteriostatic active compounds are, in particular, chitosan and phenoxyethanol. 5-Chloro-2-(2,4-dichlorophenoxy)-phenol, which is marketed by Ciba-Geigy, Basle/CH under the brand name IrgasanΣ, has also proved to be particularly effective. Suitable germ-inhibiting agents are in principle all substances which are active against Gram-position bacteria, such as e.g. 4-hydroxybenzoic acid and its salts and esters, N-(4-chlorophenyl)-N'-(3,4-dichlorophenyl)urea, 2,4,4'-trichloro-2'-hydroxydiphenyl ether (triclosan), 4-chloro-3,5-dimethylphenol, 2,2'-methylene-bis(6-bromo-4-chlorophenol), 3-methyl-4-(1-methylethyl)phenol, 2-benzyl-4-chlorophenol, 3-(4-chlorophenoxy)-1,2-propanediol, 3-iodo-2-propynyl butylcarbamate, chlorhexidine, 3,4,4'-trichlorocarbanilide (TTC), antibacterial odoriferous substances, thymol, thyme oil, eugenol, clove oil, menthol, mint oil, farnesol, phenoxyethanol, glycerol monocaprate, glycerol monocaprylate, glycerol monolaurate (GML), diglycerol monocaprate (DMC), and salicylic acid N-alkylamides, such as e.g. salicylic acid n-octylamide or salicylic acid n-decylamide.

Perspiration-Absorbing Substances:

Perspiration-absorbing substances are, for example, modified starch, such as e.g. Dry Flo Plus (National Starch), silicates, talc and other substances of similar modification which appear suitable for absorption of perspiration. The preparations according to the invention can contain the perspiration-absorbing substances in amounts of from 0.1 to 30, preferably 1 to 20 and in particular 2 to 8 wt. %—based on the total weight of the cosmetic and/or pharmaceutical preparation.

The pigments are present in finely divided form in the pigment preparations and accordingly conventionally have average particle sizes of from 0.02 to 5 Σm.

The organic pigments are conventionally organic colored and black pigments. Inorganic pigments can likewise be color pigments (colored, black and white pigments) as well as pearlescent pigments and the inorganic pigments conventionally employed as fillers.

Pigments, in particular with color-imparting properties which can be employed are iron oxides, titanium oxide, synthetic fluorphlogopite and titanium oxide, mica and/or zinc oxide.

The invention also provides lotions. In one alternative a lotion according to the invention, in particular sunscreen composition, contains or consists (of) the following components:
composition according to the invention 1-10%, preferably 4-6%;
emulsifiers 0.5-5%, preferably 1.5-3%;
emollients, preferably various emollients are employed, the proportion of which in total is 20-50%, preferably 25-35%;
UV filters, preferably various filters are employed, the proportion of which in total is 10-35%, preferably 20-25%;
demineralized water 5-50%, preferably 20-30%;
and further additives, preferably various selected from the group of those disclosed above, so that the total of all the ingredients gives 100%.

In a further alternative a lotion according to the invention contains or consists (of) the following components:
composition according to the invention 0.1-5%, preferably 1-2%;
emulsifiers 0.01-5%, preferably 0.1-1%;
emollients, preferably various emollients are employed, the proportion of which in total is 1-20%, preferably 5-12%;
agents which impart consistency and thickening agents, preferably various agents are employed, the proportion of which in total is 0.5-10%, preferably 2-5%;
rheology substances 0.01-5%, preferably 0.1-1%;
antioxidants 0.01-10%, preferably 0.1-1%;
humectant 1-10%, preferably 2-8%, particularly preferably 4-6%;
demineralized water 50-90%, preferably 75-85%;
and further additives, preferably various selected from the group of those disclosed above, so that the total of all the ingredients gives 100%.

The invention also provides creams. In a further alternative a cream according to the invention contains or consists (of) the following components:
composition according to the invention 0.1-10%, preferably 2-5%;
emulsifiers 0.01-5%, preferably 0.1-1%;
emollients, preferably various emollients are employed, the proportion of which in total is 1-30%, preferably 10-20%;
agents which impart consistency and thickening agents, preferably various agents are employed, the proportion of which in total is 0.1-10%, preferably 1.5-5%;
rheology substances 0.01-5%, preferably 0.1-1%;
humectant 1-10%, preferably 2.5-5%;
demineralized water 50-90%, preferably 70-80%;
and further additives, preferably various selected from the group of those disclosed above, so that the total of all the ingredients gives 100%.

The invention also provides a body butter. In a further alternative a body butter according to the invention contains or consists (of) the following components and optionally further auxiliary substances:
composition according to the invention 0.1-10%, preferably 1-5%;
emulsifiers 0.01-5%, preferably 0.1-1%;
emollients, preferably various emollients are employed, the proportion of which in total is 5-40%, preferably 20-25%;
agents which impart consistency and thickening agents, preferably various agents are employed, the proportion of which in total is 0.5-20%, preferably 5-10%;
rheology substances 0.01-5%, preferably 0.1-1%;
humectant 1-10%, preferably 2.5-7.5%;
demineralized water 40-80%, preferably 60-70%;
antioxidants 0.01-5%, preferably 0.1-1%;
and further additives, preferably various selected from the group of those disclosed above, so that the total of all the ingredients gives 100%.

The invention also provides products of decorative cosmetics, such as, for example
lipstick, lip gloss, eye shadow, powder, rouge, make-up, concealer, eyeliner, mascara, kajal, and
BB (blemish balm) products, such as, for example, BB creams, BB foundations, BB concealer.

In one alternative a BB (blemish balm) product according to the invention contains or consists (of) the following components, so that the total of all the ingredients gives 100%:

purified water: to 100%, butylene glycol: 1-10%, preferably 2-6%, iron oxides: 0.01-5%, preferably 0.1-1%, titanium oxide: 1-10%, preferably 3-7%, xanthan gum: 0.01-2%, preferably 0.05-1.0%, composition according to the invention: 1-10%, preferably 2-8%, disodium cetearyl sulfosuccinate: 0.1-5%, preferably 1-3%, diethylaminohydroxybenzoyl hexyl benzoate: 1-10%, preferably 2-6%, methylenebisbenzotriazolyltetramethylbutylphenol: 1-10%, preferably 2-6%, octinoxate: 1-10%, preferably 2-8%, bisethylhexyloxyphenolmethoxyphenyltriazine: 0.1-5%, preferably 0.5-3%, dicaprylyl carbonate: 1-20%, preferably 2-15%, cyclomethicone: 1-10%, preferably 2-8%, propylene carbonate: 0.1-5%, preferably 0.2-2%, stearalkonium hectorite: 0.1-10%, preferably 0.5-3%, synthetic fluorphlogopite and titanium oxide: 0.5-6%, preferably 1-3%, mica: 1-10%, preferably 2-6%, zinc oxide: 10-30%, preferably 15-25%, talc: 1-10%, preferably 2-8%, sodium polyacrylate: 0.1-5%, preferably 0.5-.26%, acrylate/methacrylamide copolymer: 1-10%, preferably 2-6%.

The invention also provides a BB (blemish balm) body cream, in particular sunscreen composition. In a further alternative a body cream according to the invention contains or consists (of) the following components and optionally further auxiliary substances, so that the total of all the ingredients gives 100%:
composition according to the invention 0.1-20%, preferably 1-10%;
emulsifiers 0.01-5%, preferably 0.1-2%;
emollients, preferably various emollients are employed, the proportion of which in total is 5-40%, preferably 10-30%;
filler 0.5-20%, is preferably 1-10%;
UV filters, preferably various emollients are employed, the proportion of which in total is 1-40%, preferably 10-30%;
rheology substances 0.01-5%, preferably 0.1-2%;
humectant 0.1-10%, preferably 1-5%;
demineralized water 30-80%, preferably 40-50%;
effect pigments, preferably various emollients are employed, the proportion of which in total is 0.1-10%, preferably 1-7%;
preservatives 0.01-5%, preferably 0.1-2%;

The invention also provides a BB (blemish balm) cream, in particular sunscreen composition. In a further alternative a cream according to the invention contains or consists (of) the following components and optionally further auxiliary substances, so that the total of all the ingredients gives 100%:
composition according to the invention 0.1-20%, preferably 1-10%;
emulsifiers 0.01-8%, preferably 0.1-3%;
emollients, preferably various emollients are employed, the proportion of which in total is 5-40%, preferably 10-30%;
filler 0.5-10%, is preferably 1-5%;
UV filters, preferably various emollients are employed, the proportion of which in total is 1-40%, preferably 10-20%;
rheology substances 0.01-10%, preferably 0.1-5%;
humectant 0.1-15%, preferably 2-10%;
demineralized water 20-70%, preferably 30-50%;
effect pigments, preferably various emollients are employed, the proportion of which in total is 0.1-10%, preferably 1-5%;
dyestuffs, preferably various emollients are employed, the proportion of which in total is 0.1-15%, preferably 2-10%;
preservatives 0.01-5%, preferably 0.1-2%;

The invention also provides a face mask. In a further alternative a face mask according to the invention contains or consists (of) the following components and optionally further auxiliary substances:
composition according to the invention 0.1-10%, preferably 1-5%;
emulsifiers 0.01-5%, preferably 0.1-1%;
emollients, preferably various emollients are employed, the proportion of which in total is 5-30%, preferably 10-20%;
agents which impart consistency and thickening agents, preferably various agents are employed, the proportion of which in total is 0.5-15%, preferably 2-5%;
rheology substances 0.01-5%, preferably 0.1-1%;
humectant 1-10%, preferably 2-8%;
demineralized water 50-90%, preferably 65-75%;
and further additives, preferably various selected from the group of those disclosed above, so that the total of all the ingredients gives 100%.

The invention also provides a hand cream. In a further alternative a hand cream according to the invention contains or consists (of) the following components and optionally further auxiliary substances, containing the composition according to the invention and further auxiliary substances:
composition according to the invention 0.1-10%, preferably 1-5%;
emulsifiers 0.01-5%, preferably 0.1-1%;
emollients, preferably various emollients are employed, the proportion of which in total is 1-20%, preferably 2-15%;
agents which impart consistency and thickening agents, preferably various agents are employed, the proportion of which in total is 0.5-15%, preferably 2-5%;
rheology substances 0.01-5%, preferably 0.1-1%;
humectant 1-30%, preferably 2 5-20%;
demineralized water 50-90%, preferably 65-75%;
and further additives, preferably various selected from the group of those disclosed above, so that the total of all the ingredients gives 100%.

The invention also provides a serum. In a further alternative a serum according to the invention contains or consists (of) the following components and optionally further auxiliary substances, containing the composition according to the invention and further auxiliary substances:
composition according to the invention 0.1-10%, preferably 1-5%;
emulsifiers 0.01-5%, preferably 0.1-1%;
emollients, preferably various emollients are employed, the proportion of which in total is 1-20%, preferably 2-10%;
agents which impart consistency and thickening agents, preferably various agents are employed, the proportion of which in total is 0.1-10%, preferably 0.5-2%;
rheology substances 0.01-5%, preferably 0.1-1%;
humectant 0.1-10%, preferably 1-5%;
demineralized water 60-95%, preferably 80-90%;
and further additives, preferably various selected from the group of those disclosed above, so that the total of all the ingredients gives 100%.

In a further alternative cosmetic products, in particular of decorative cosmetics, are selected from the following tables:

The total proportion of the auxiliary substances and additives can be 1 to 50, preferably 5 to 40 wt. %, based on the compositions. The compositions can be prepared by conventional cold or hot processes. The compositions can be prepared by the phase inversion temperature method.

The composition according to the invention, the shaped body according to the invention and the process according to the invention display outstanding sensorial properties and render possible the use of sustainable and/or renewable raw materials. These are raw materials which are not produced petrochemically and which are of plant or animal origin and can be utilized as substances or energy outside the field of nutrition (foodstuffs and feedstuffs).

In particular in the preparation according to the invention of carbohydrate partial esters with an acyl component in which R1 is an alkyl and/or alkene having a carbon length of C16 and/or C18, sustainable and/or renewable (biologically renewable) raw materials are employed. Consequently, cetearyl methyl esters, in one embodiment obtained from palm oil, are employed for the esterification or transesterification.

The process according to the invention can advantageously be applied—both on a laboratory scale and, without modifications—on an industrial scale. That is to say transfer of the individual process steps from the laboratory scale into the industrial scale can take place without further effort, although temperature variations of +/−10° C. are possible in processes on an industrial scale. In other processes which are not according to the invention such temperature variations can lead to significant changes in the yield and in particular in the composition of the products.

In the context of the invention on an industrial scale the processes are those in which the educts, in particular carbohydrates and the alkyl esters employed for the esterification, are employed in an amount of in each case more than 1 kg, preferably at least 5 kg, at least 10 kg, particularly preferably at least 25 kg, 50 kg, in particular at least 100 kg.

The present invention thus also provides cosmetic products which meet the requirements according to Ecocert for natural cosmetics and bio natural cosmetics:

Ecocert natural cosmetics
At least 95% of all the ingredients are of natural origin.
At least 5% of all the ingredients in the end product originate from biological cultivation
At least 50% of the plant substances employed originate from biological cultivation
Synthetic dyestuffs and fragrances, synthetic fats, oils, silicones and crude oil products are not permitted
No animal studies with the finished product
Use of animal raw materials only from live animals
Only certain substances are permitted for preserving
Ban on raw materials manipulated by genetic engineering
No radioactive irradiation for sterilizing raw materials or products
Ecocert biological natural cosmetics: Compared with merely natural cosmetics, higher contents of ingredients from controlled biological cultivation are specified here:
At least 95% of all the ingredients are of natural origin
At least 10% of all the ingredients originate from biological cultivation
At least 95% of the plant substances employed originate from biological cultivation
Synthetic dyestuffs and fragrances, synthetic fats, oils, silicones and crude oil products are not permitted
No animal studies with the finished product
Use of animal raw materials only from live animals
Only certain substances are permitted for preserving
Ban on raw materials manipulated by genetic engineering
No radioactive irradiation for sterilizing raw materials or products

EXAMPLES

1. According to the Invention

Sucrose ester was prepared according to Example 1 of EP 1 811 951 B1:

However, the working up was carried out without deactivation of the catalyst. In each case Cetyl Palmitate, Hexyldecyl Stearate and hydrogenated palm oil was added as an emollient at 100° C.

After decanting at 100° C. by means of a centrifuge or decanter, bleaching was carried out by means of 35% strength H2O2 solution. An almost colorless solid was present at room temperature.

GPC analyses showed no change in the carbohydrate partial ester distribution between the crude and end product.

Figure 2:
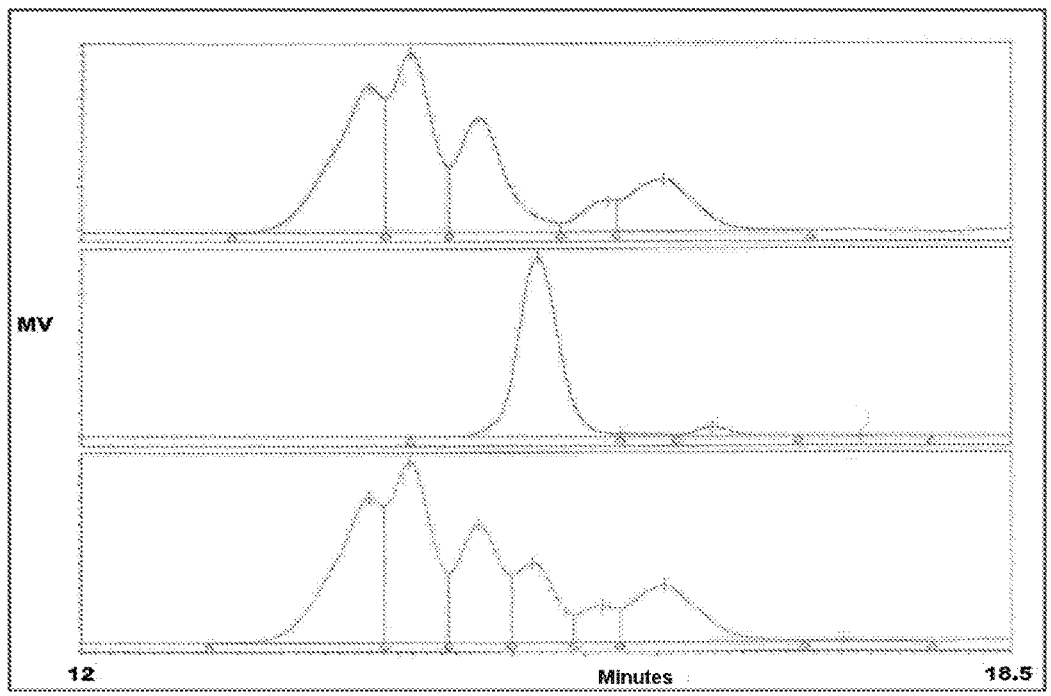
Figure 3:
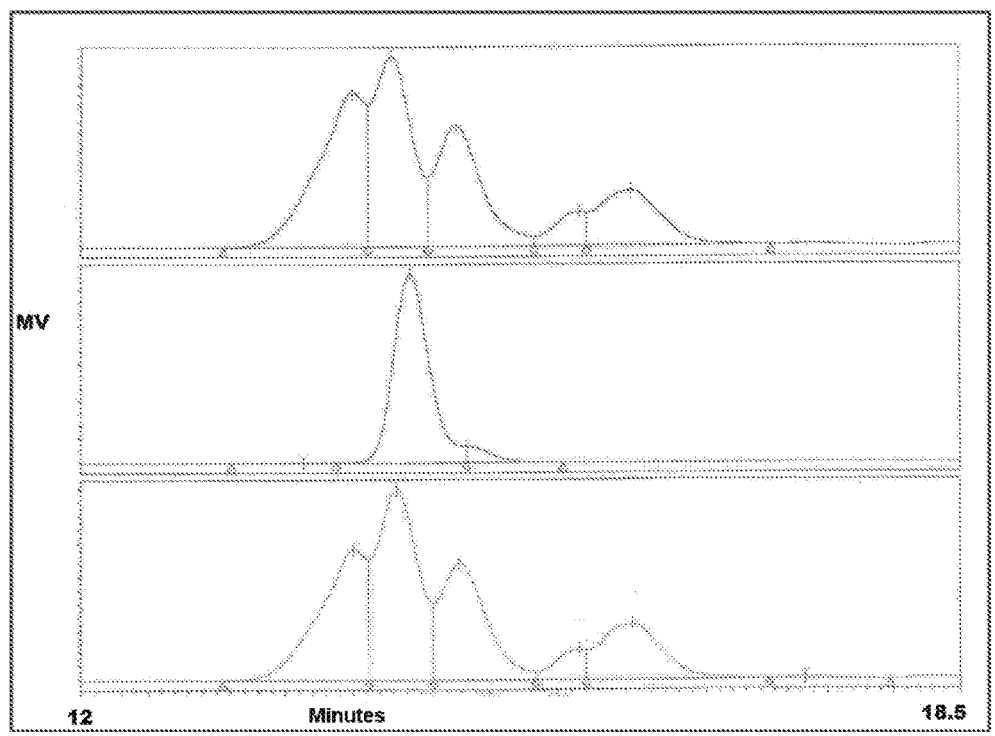

Emollient (Ester Oil):
Cetyl Palmitate in FIG. 1, Hexyldecyl Stearate in FIG. 2 and hydrogenated palm oil in FIG. 3.

The figures each show the GPC of the particular crude product from step i) of the process according to the invention in the top diagram, the middle diagram shows the GPC of the particular pure emollient and the bottom diagram shows the GPC of the particular end product.

The pastilles produced from the end product were hard but not brittle. No "sweating" was observed, even during storage for longer than one week at 40° C. The pastilles also did not become tacky in the storage test.

Example 2: Synthesis of a Product According to the Invention on an Industrial Scale Sucrose Polystearate with Cutina CP
a) Synthesis:
393 kg of molten methyl ester (Edenor ME AS 16V, cetearyl methyl ester, BASF) were initially introduced at 70° C. into a reactor with heating, a stirrer, a vacuum apparatus and a nitrogen feed, the container was rendered inert with nitrogen and 16.3 g of potassium carbonate, 124 kg of Sisterna SP-30C (sucrose distearate), 266 kg of powdered sugar and 1.3 kg of sodium hypophosphite were added in succession with thorough mixing. After removal of water (90 min at 85° C., 5 mbar) the mixture was heated up slowly to 135° C. and the methanol formed was removed in vacuo. The reaction was ended at a content of methyl palmitate in the reaction mixture of less than 3%. The crude product was cooled to 100° C. and 85 kg of cetyl palmitate (Cutina CP) was stirred in.
b) Working Up:
The residual sugar content in the product was lowered to 3.8% by separating off the unreacted sugar by means of a decanter (for example decanting centrifuge from Siebtechnik, TS 210) (nitrogen atmosphere, 100° C.).

A subsequent filtration (approx. 10 kg of filtering aid Seitz Ultra, filter sheets K900, Pall, nitrogen atmosphere, 100° C.) lowered the residual sugar content (determined by means of GC) only to 3.4%.

GPC analysis delivered the same result as shown in FIG. 1.

For bleaching the product was in a suitable reactor at 75-80° C. under a nitrogen atmosphere and 6 kg of hydrogen peroxide (35% strength) was added slowly with thorough stirring such that excessive foaming and an increase in temperature above 90° C. were avoided. The mixture was subsequently stirred for approx. 60 min until the peroxide number was below 5 mmol of $O_2$/kg.

3. Comparative Example

Figure 4:
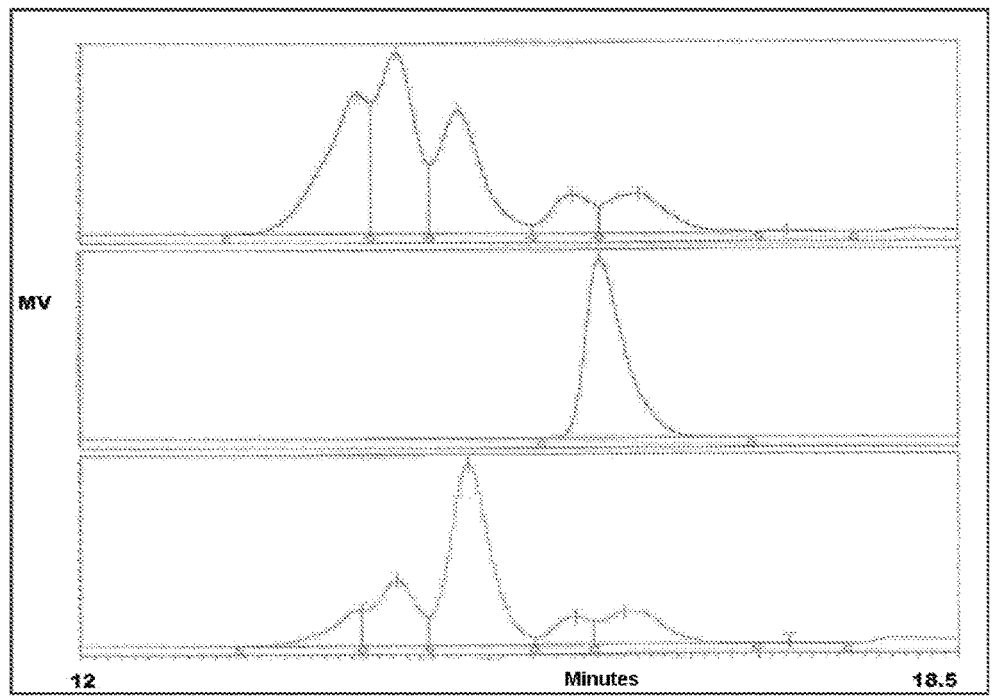

The comparative examples were carried out analogously to Example 1. However, behenyl alcohol in FIG. 4 and Caprylic/Capric Triglyceride (Myritol 312) in FIG. 5 were each employed as emollients.

GPC analyses showed different carbohydrate partial ester distributions in each case between the crude and end product.

4. Comparative Example on an Industrial Scale

The synthesis of a product which is not according to the invention was carried out as described in Example 2; instead of Cutina CP, however, 90 kg of Myritol 312 were used as the ester oil.

Figure 5:
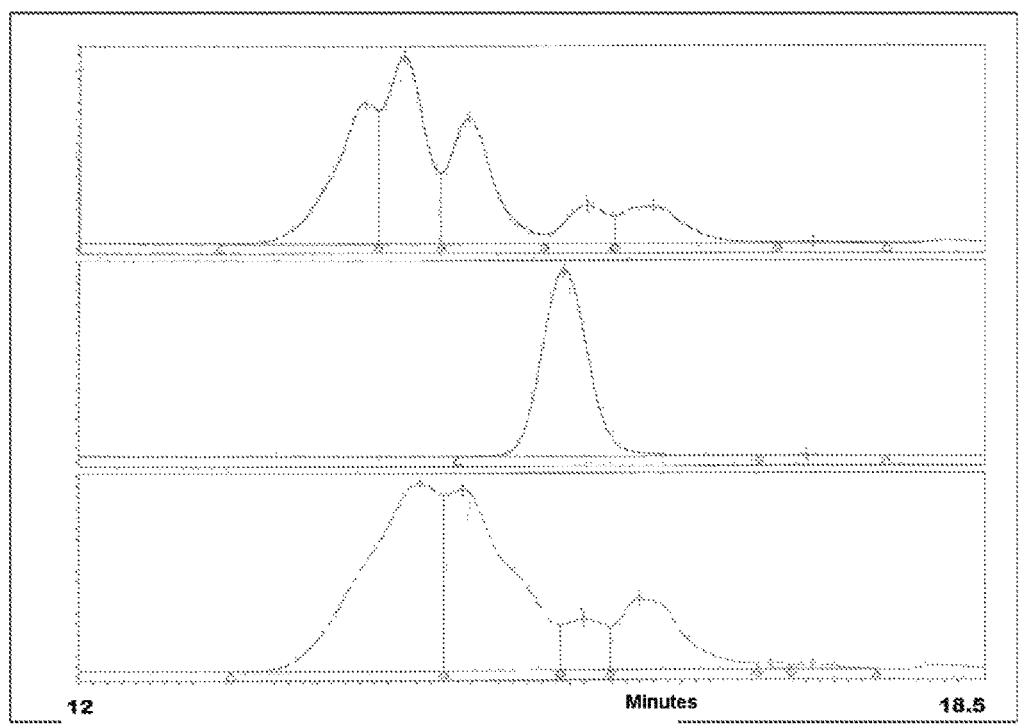

In the course of the working up the residual sugar content after filtration could be lowered to 2.4%. However, the end product shows a significantly changed ester distribution, as in FIG. 5, compared with the crude ester.

The ester composition of the sucrose ester changed significantly during the working up when a $C_{8-10}$-triglyceride was used as the ester oil, so that the object of the invention is not achieved.

Corresponding experiments analogously to Example 4 and 5 can also be carried out with further ester oils (emollients) which are not to be employed according to the invention, such as, for example, with ester oils in which the alcohol component R3 is methyl or ethyl, or other alkyls having a chain length of less than 8 carbon atoms.

5. Alcohol Content in Products According to the Invention

The transfer of the acid group of an ester oil according to the invention to the sucrose ester is accompanied by the liberation of the corresponding alcohol radical of the diluent. When an ester oil to be employed according to the invention, such as Cutina CP, is used, after splitting thereof a mixture of palmityl and stearyl alcohol would thus have to be detectable in the end product; for example by gas chromatography.

In the context of a stability study, the product according to the invention was stored at 120° C. for 24 hours.

The GCs of the start and end material of this study show no bands of palmityol and stearyl alcohol even after 24 h.

6. Decanting

Example 1 and 2 show that in the process according to the invention decanting for separating off the sugar residue delivered satisfactory results (=residual sugar contents). A time-consuming filtration of the crude product therefore is not necessary. A filtration after a decanting moreover lowered the residual sugar content further only insignificantly.

The invention claimed is:

1. A composition containing:
a1) carbohydrate partial esters as the product of an esterification of at least one hydroxy group of a carbohydrate with acyl components of the formula R1-COO,
b1) alkyl esters of the formula R1-COO-R2, and
c1) ester oils of the formula R1-COO-R3,
and optionally carbohydrates, catalyst, fatty acids, and/or fatty soaps;
wherein:
the acyl component R1 is selected from the group consisting of mono- and di-acids of chain length C14-C22 and combinations thereof,
the alcohol component R2 of the ester b1) is a C1 to C3 alcohol unit,
the ester oils c1) have an alcohol component R3 selected from the group consisting of branched alcohols with C8-C22, unbranched alcohols with C8-C22, polyalcohols, and mixtures thereof, the alcohol component R3 being completely esterified with the acyl component R1, and
the composition contains no free alcohol component of the ester oils c1).

2. A composition containing:
a2) carbohydrate partial esters having an average degree of esterification of 1-4,
b2) organic alkyl esters with an acyl component having 14-22 carbon atoms and an alcohol component of the ester b2) is a C1 to C3 alcohol unit, and
c2) ester oils with a linear acyl component having 14-22 carbon atoms and a linear alcohol component having 8-22 carbon atoms,
and optionally carbohydrates, catalyst, fatty acids, and/or fatty soaps;
wherein the composition contains no free alcohol component of the ester oils c2).

3. The composition according to claim 1, wherein the product a1) is a glycose partial ester after esterification with an acyl component of b1).

4. The composition according to claim 3, wherein the glycoses are mono- and/or disaccharides.

5. The composition according to claim 1, wherein the acyl component of the ester a1), b1), c1) is a fatty acid radical having 16 or 18 carbon atoms.

6. The composition according to claim 1, wherein the alcohol component of the ester oils c1) is a fatty alcohol having 16 or 18 carbon atoms.

7. The composition according to claim 1, wherein the alcohol component of the ester oils c1) is a Guerbet alcohol having 16 to 20 carbon atoms or a polyalcohol selected from the group consisting of ethylene glycol, propylene glycol, butylene glycol, neopentyl glycols, and glycerol, and the ester oils c1) are completely esterified.

8. The composition according to claim 1, wherein the carbohydrate partial ester contains
monoester in a proportion of from 0% to 20% by weight,
diester in a proportion of from 10% to 40% by weight,
triester in a proportion of from 20% to 50% by weight, and
tetraester in a proportion of from 15% to 40% by weight,
wherein the total is 100% by weight.

9. The composition according to claim 1, wherein the ratio of monoester:diester:triester:tetraester is between 0.5 and 1.5:between 3.0 and 4.0:between 4.0 and 5.0:between 3.0 and 4.0.

10. A shaped body comprising a composition according to claim 1.

11. A process for the preparation of a composition according to claim 1, the process comprising:
i) esterifying or transesterifying a carbohydrate with an alkyl ester b1) in the presence of a catalyst to form carbohydrate partial esters a1) as an esterification or transesterification product,
ii) adding ester oils c1) to the esterification or transesterification product to form a crude product,
iii) separating residual unreacted carbohydrate from the crude product to form the composition according to claim 1,
optionally iv) bleaching the composition, and
optionally v) forming a shaped body from the composition.

12. The process according to claim 11, wherein no deactivation of the catalyst is carried out.

13. The process according to claim 11, wherein the esterification or transesterification product from step i) has the same carbohydrate partial ester distribution as the composition from step iii), iv) or v).

14. A cosmetic and/or pharmaceutical product and/or foodstuff containing a composition according to claim 1.

15. The composition according to claim 2, wherein the product a2) is a glycose partial ester after esterification with an acyl component of b2).

16. The composition according to claim 2, wherein the acyl component of the ester a2), b2) or c2) is a fatty acid radical having 16 or 18 carbon atoms.

17. The composition according to claim 2, wherein the alcohol component of the ester oils c2) is a fatty alcohol having 16 or 18 carbon atoms.

18. The composition according to claim 2, wherein the carbohydrate partial ester contains
   monoester in a proportion of from 0% to 20% by weight,
   diester in a proportion of from 10% to 40% by weight,
   triester in a proportion of from 20% to 50% by weight, and
   tetraester in a proportion of from 15% to 40% by weight,
   wherein the total is 100% by weight.

19. A shaped body comprising a composition according to claim 2.

20. The process according to claim 11, wherein the acyl component R1 of the ester a1), b1), or c1), is a fatty acid radical having 16 or 18 carbon atoms.

* * * * *